(12) United States Patent
Depreux et al.

(10) Patent No.: US 6,310,074 B1
(45) Date of Patent: Oct. 30, 2001

(54) SUBSTITUTED DIMERIC COMPOUNDS

(75) Inventors: Patrick Depreux, Armentieres; Said Yous, Lille; Gwenael Cheve, La Madeleine; Gérald Guillaumet, Saint Jean le Blanc; Marie-Claude Viaud; Carlos Larraya, both of Tours; Caroline Bennejean, Charenton le Pont; Philippe Delagrange, Issy les Moulineaux; Pierre Renard, Le Chesnay; Carole Descamps-Francois, Hellemes, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/573,704

(22) Filed: May 18, 2000

(30) Foreign Application Priority Data

May 19, 1999 (FR) .................................................. 99.06331

(51) Int. Cl.[7] .......................... A61K 31/38; A61K 31/40; C07D 307/81; C07D 333/58; C07D 409/12
(52) U.S. Cl. .......................... 514/300; 514/419; 514/443; 514/469; 514/598; 514/616; 546/113; 546/114; 546/116; 548/454; 549/52; 549/55; 549/57; 549/58; 549/366; 549/407; 549/467; 560/28; 560/34; 560/42; 562/439; 562/442; 564/56; 564/158
(58) Field of Search .......................... 546/113; 548/507, 548/454; 549/52, 55, 467, 58, 57; 564/158, 56; 514/300, 419, 443, 469, 616, 598; 560/28, 34, 42

(56) References Cited

U.S. PATENT DOCUMENTS 5,616,614 * 4/1997 Yous et al. .......................... 514/530

* cited by examiner

Primary Examiner—Bernard Dentz
(74) Attorney, Agent, or Firm—The Firm of Hueschen and Sage; G. Patrick Sage

(57) ABSTRACT

The invention relates to compound of formula (I):

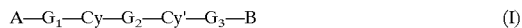

(I)

wherein:

A represents a grouping $NR^1C(Q)R^2$, $C(Q)NR^2R^3$ or $NR^1C(Q)NR^2R^3$,

B represents a grouping $NR^1C(Q)R^2$, $NR^1C(Q)NR^2R^3$, $C(Q)NR^2R^3$, $C(Q)OR^1$, $NR^1C(Q)OR^2$ or $NR^2R^3$, $G_1$ and $G_3$ represent an optionally substituted alkylene chain, Cy and Cy', which are different, represent a ring structure

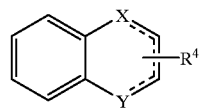

or

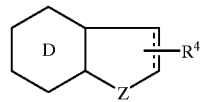

$G_2$ represents a chain

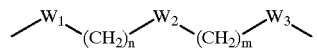

and medicinal products containing the same are useful in treating or in preventing melatoninergic disorders.

13 Claims, No Drawings

SUBSTITUTED DIMERIC COMPOUNDS

FIELD OF THE INVENTION

The present invention relates to new substituted dimeric compounds. Owing to their novel structure, the compounds of the present invention are new and have pharmacological properties that are very valuable in respect of melatoninergic receptors.

1. Description of the Prior Art

From the prior art dimeric structures are known in the naphthalene series (J. Chem. Soc., Dalton Trans., 1979, (10), pp. 1497–502) that have been studied for their coordination properties in metal complexes, or in the indole series studied for their "curare-like" activity (Khim.-Farm. Zh., 1984, 18 (1), pp. 29–31). Moreover, Applications WO 9600720 and WO 9414771 describe mixed dimeric structures for use as 5-$HT_1$ ligands and synthesis intermediates, respectively.

2. Background of the Invention

Numerous studies in the last ten years have demonstrated the key role of melatonin (N-acetyl-5-methoxytryptamine) in many physiopathological phenomena and in the control of the circadian rhythm. Its half-life is quite short, however, owing to the fact that it is rapidly metabolised. Great interest therefore lies in the possibility of providing the clinician with melatonin analogues that are metabolically more stable, have an agonist or antagonist character and that may be expected to have a therapeutic effect that is superior to that of the hormone itself.

In addition to their beneficial action on circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272) and analgesic properties (Pharmacopsychiat., 1987, 20, pp. 222–223) as well as for the treatment of Parkinson's disease (J. Neurosurg. 1985. 63, pp. 321–341) and Alzheimer's disease (Brain Research, 1990, 528, pp. 170–174). Those compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20 (4), pp. 443–446).

Those various effects are exerted via the intermediary of specific melatonin receptors. Molecular biology studies have demonstrated the existence of a number of receptor sub-types that are capable of binding that hormone (Trends Pharmacol. Sci., 1995, 16, p 50; WO 97.04094). It has been possible, for various species, including mammals, for some of those receptors to be located and characterised. In order to be able to understand the physiological functions of those receptors better, it is of great advantage that specific ligands are available. Moreover, such compounds, by interacting selectively with one or other of those receptors, may be excellent medicaments for the clinician in the treatment of pathologies associated with the melatoninergic system, some of which have been mentioned above.

In addition to the fact that the compounds of the present invention are new, they show very strong affinity for melatonin receptors and/or selectivity for one or other of the melatoninergic receptor sub-types.

DETAILED DESCRIPTION OF THE INVENTION

The present invention relates more especially to compounds of formula (I):

$$A-G_1-Cy-G_2-Cy'-G_3-B \quad (I)$$

wherein:

A represents grouping of formula

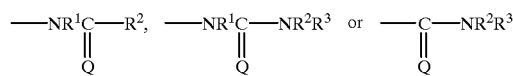

wherein:

Q represents a sulphur or oxygen atom, $R^1$, $R^2$ and $R^3$, which may be identical or different, represent a hydrogen atom or a group $R_a$ (wherein $R_a$ represents an unsubstituted or substituted linear or branched ($C_1$–$C_6$)alkyl group, an unsubstituted or substituted linear or branched ($C_2$–$C_6$)alkenyl group, an unsubstituted or substituted linear or branched ($C_2$–$C_6$)alkynyl group, an unsubstituted or substituted ($C_3$–$C_8$)cycloalkyl group, an unsubstituted or substituted cycloalkyl-($C_3$–$C_8$)alkyl group in which the alkyl moiety is linear or branched, a polyhalo-($C_1$–$C_6$)alkyl group in which the alkyl moiety is linear or branched, an aryl group, an aryl-($C_1$–$C_6$)alkyl group in which the alkyl moiety is linear or branched, an aryl-($C_2$–$C_6$)alkenyl group in which the alkenyl moiety is linear or branched, a heteroaryl group, a heteroaryl-($C_1$–$C_6$)alkyl group in which the alkyl moiety is linear or branched or a heteroaryl-($C_2$–$C_6$)alkenyl group in which the alkenyl moiety is linear or branched), or the groups $R^2$ and $R^3$ can also form with the nitrogen atom carrying them a group selected from piperazinyl, piperidinyl and pyrrolidinyl, B represents a grouping of formula

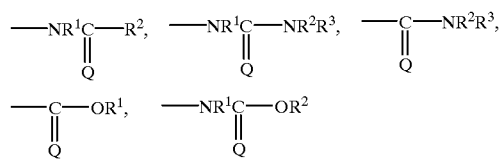

or $-NR^2R^3$ wherein Q, $R^1$, $R^2$ and $R^3$ are as defined hereinbefore, $G_1$ and $G_3$, which may be identical or different, represent a linear or branched alkylene chain containing from 1 to 4 carbon atoms that is optionally substituted by one or more identical or different groups selected from hydroxy, carboxy, formyl, $R_a$, $OR_a$, $COOR_a$ and $COR_a$ (wherein $R_a$ is as defined hereinbefore), Cy and Cy', which are different, represent a ring structure of formula (II):

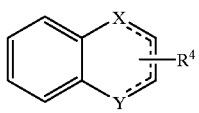

(II)

wherein:

X and Y, which may be identical or different, represent a sulphur, oxygen or carbon atom, or a CH or $CH_2$ group, $R^4$ represents a hydrogen or halogen atom, or a $CF_3$, hydroxy, carboxy, formyl, amino, $NHR_a$, $NR_aR^1_a$, NHCOR$_a$, CONHR$_a$, R$_a$, OR$_a$, COR$_a$ or COOR$_a$ group, (wherein R$_a$ is as defined hereinbefore and R$^1_a$ can have any of the meanings of R$_a$), the symbol ═══ means that the bonds are single or double, with the proviso that the valency of the atoms is respected, wherein G$_2$ substitutes the benzene ring, and G$_1$ substitutes the ring containing X and Y in the case of Cy, and G$_2$ substitutes the benzene ring and G$_3$ substitutes the ring containing X and Y in the case of Cy', or a ring structure of formula (III):

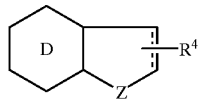

(III)

wherein:

Z represents a sulphur or oxygen atom, or a CH$_2$, NH, NSO$_2$Ph or NR$_a$ group (wherein R$_a$ is as defined hereinbefore), D represents a benzene or pyridine ring, R$^4$ is as defined hereinbefore, the symbol ═══ means that the bond is single or double, with the proviso that the valency of the atoms is respected, wherein G$_2$ substitutes the D ring, and G$_1$ substitutes the ring containing Z in the case of Cy, and G$_2$ substitutes the D ring and G$_3$ substitutes the ring containing Z in the case of Cy', the two, different, rings Cy and Cy' of the compounds of formula (I) both being represented by a structure of formula (II) or by a structure of formula (III), or one of the two rings being represented by a structure of formula (II) and the other being represented by a structure of formula (III), G$_2$ represents a chain of formula (IV):

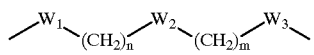

(IV)

wherein:

W$_1$, W$_2$ and W$_3$, which may be identical or different, represent a bond, an oxygen or sulphur atom, or a CH$_2$, CHR$_a$, NH or NR$_a$ group (wherein R$_a$ is as defined hereinbefore), n represents an integer wherein $0 \leq n \leq 6$, m represents an integer wherein $0 \leq m \leq 6$, with the proviso that it is not possible to have two consecutive hetero atoms and that the chain of formula (IV) so defined may have one or more unsaturated bonds, it being understood that:

"aryl" is understood to mean the groups naphthyl, phenyl and biphenyl,

"heteroaryl" is understood to mean any saturated or unsaturated mono- or bi-cyclic group containing from 5 to 10 ring atoms and containing from 1 to 3 hetero atoms selected from nitrogen, sulphur and oxygen, it being possible for the "aryl" and "heteroaryl" groups to be substituted by one or more identical or different radicals selected from hydroxy, carboxy, linear or branched (C$_1$–C$_6$)alkoxy, linear or branched (C$_1$–C$_6$)

alkyl, polyhalo-(C$_1$–C$_6$)-alkyl in which the alkyl moiety is linear or branched, formyl, cyano, nitro, amino, linear or branched (C$_1$–C$_6$)alkylamino, di-(C$_1$–C$_6$)alkylamino in which each alkyl moiety is linear or branched and halogen atoms, the term "substituted" applied to the terms "alkyl", "alkenyl" and "alkynyl" means that those groups are substituted by one or more identical or different radicals selected from hydroxy, linear or branched (C$_1$–C$_6$)alkoxy, polyhalo-(C$_1$–C$_6$)alkyl in which the alkyl moiety is linear or branched, amino, linear or branched (C$_1$–C$_6$)alkylamino, di-(C$_1$–C$_6$)alkylamino in which each alkyl moiety is linear or branched and halogen atoms, the term "substituted" applied to the terms "cycloalkyl" and "cycloalkylalkyl" means that the cyclic moiety of those groups is substituted by one or more identical or different radicals selected from hydroxy, linear or branched (C$_1$–C$_6$)alkoxy, polyhalo-(C$_1$–C$_6$) alkyl in which the alkyl moiety is linear or branched, amino, linear or branched (C$_1$–C$_6$)alkylamino, di-(C$_1$–C$_6$)alkylamino in which each alkyl moiety is linear or branched and halogen atoms, their enantiomers and diastereoisomers, and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid. glutaric acid, fumaric acid, tartaric acid, maleic acid, citric acid, ascorbic acid. methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The preferred compounds of the invention are the compounds of formula (I) wherein:

Cy and Cy', which are different, represent a ring structure of formula (II), such as, for example, naphthalene, tetrahydronaphthalene, the groups 1,4-benzodioxine or chroman, Cy and Cy', which are different, represent a ring structure of formula (III), such as, for example, indole, azaindole, benzothiophene or benzofuran, Cy represents a ring structure of formula (II) and Cy' represents a ring structure of formula (III).

Advantageously, the invention relates to compounds of formula (I) wherein G$_2$ represents a single bond, or a grouping —W$_4$—(CH$_2$)$_p$—W'$_4$— (wherein W$_4$ and W'$_4$, which may be identical or different, represent an oxygen or sulphur atom, or an NH or NR$_a$ group, and p represents an integer wherein $1 \leq p \leq 12$), such as, for example, the grouping —O—(CH$_2$)$_p$—O— (wherein p is as defined hereinbefore), or a grouping of formula —W$_4$—(CH$_2$)$_{p'}$—W'$_4$—(CH$_2$)$_{p''}$—W''$_4$— (wherein W$_4$, W'$_4$ and W''$_4$, which may be identical or different, represent an oxygen or sulphur atom, or an NH or NR$_a$ group, and p' and p'' are two integers wherein $2 \leq p'+p'' \leq 12$), such as, for example, the grouping —O—(CH$_2$)$_{p'}$—O—(CH$_2$)$_{p''}$—O— (wherein p' and p'' are as defined hereinbefore).

Preferred substituents A and B of the invention are the groupings NR$^1$C(Q)R$^2$, NR$^1$C(Q)NR$^2$R$^3$ and C(Q)NR$^2$R$^3$ and more especially the groupings NR$^1$COR$^2$ and CONR$^2$R$^3$.

More especially still, the invention relates to the compounds of formula (I) which are N-(2-{7-[2-({3-[2-(acetylamino)ethyl]-1-benzofuran-5-yl}oxy)ethoxy]-1-naphthyl}-ethyl)acetamide, N-(2-{5-[2-({8-[2-(acetylamino)ethyl]-2-naphthyl}oxy)ethoxy]-1-benzofur-3-yl}ethyl)-2-furamide, N-(2-{5-[2-({8-[2-(acetylamino)ethyl]-2-naphthyl}oxy)ethoxy]-1H-pyrrolo[2,3-b]-pyridin-3-yl}ethyl)cyclopropanecarboxamide, N-(2-{7-[3-({3-[2-(acetylamino)ethyl]-1-benzothiophen-5-yl}oxy)propoxy]-1-naphthyl}ethyl)acetamide, N-[2-(5-{[6-({8-[2-(acetylamino)ethyl]-2-naphthyl}oxy)hexyl]oxy}-1H-pyrrolo-[2,3-b]pyridin-3-yl)ethyl]acetamide, N-(2-{7-[4-({3-[2-(acetylamino)ethyl]-1-benzofuran-5-yl}oxy)butoxy]-1-naphthyl}-ethyl)acetamide, N-{2-[5-[4-({8-[2-(acetylamino)ethyl]-2-naphthyl}oxy)butoxy]-1-(phenylsulphonyl)-1H-indol-3-yl]ethyl}acetamide, N-(2- {7-[4-({8-[2-(acetylamino)ethyl]-2-naphthyl}oxy)butoxy]-1,2,3,4-tetrahydro-1-naphthalenyl}ethyl)acetamide, N-(2-{5-[4-({3-[2-(acetylamino)ethyl]-3a,7a-dihydro-1benzofuran-5-yl}oxy)-butoxy]-1H-indol-3-yl}ethyl)acetamide, N-(2-{7-[4-({3-[2-(acetylamino)ethyl]-1-benzothien-5-yl}oxy)butoxy]-1-naphthyl}-ethyl)acetamide, N-(2-{5-[4-({3-[2-(acetylamino)ethyl]-1-benzothien-5-yl}oxy)butoxy]-1H-indol-3-yl}ethyl)acetamide, N-(2-{5-[4-({3-[2-(acetylamino)ethyl]-1-benzothien-5-yl}oxy)butoxy]-1H-pyrrolo-[2,3-b]pyridin-3-yl}ethyl)acetamide, N-(2-{5-[4-({3-[2-(acetylamino)ethyl]-1-benzofuran-5-yl}oxy)butoxy]1H-pyrrolo-[2,3-b]pyridin-3-yl}ethyl)acetamide, N-(2-{5-[4-({3-[2-(acetylamino)ethyl]-1H-indol-5-yl}oxy)butoxy]-1H-pyrrolo[2,3-b]pyridin-3-yl}ethyl)acetamide, N-[2-(7-{3-[2-(acetylamino)ethyl]-1-benzofuran-5-yl}-1-naphthyl)ethyl]acetamide N-[3-(5-{8-[2-(acetylamino)ethyl]-2-naphthyl}-1H-pyrrolo[2,3-b]pyridin-3-yl)-propyl]heptanamide, N-[2-(7-{3-[2-(acetylamino)ethyl]-1-benzothien-5-yl}-1-naphthyl)ethyl]acetamide, N-[2-(5-{8-[2-(acetylamino)ethyl]-2-naphthyl}-1H-pyrrolo[2,3-b]pyridin-3-yl)-ethyl]acetamide, N-[2-(5-{3-[2-(acetylamino)ethyl]-1-benzofuran-5-yl}-1-benzothien-3-yl)ethyl]-acetamide, N-[2-(5-{3-[2-(acetylamino)ethyl]-1-benzofuran-5-yl}-1H-indol-3-yl)ethyl]-acetamide, N-[2-(5-{3-[2-(acetylamino)ethyl]-1-benzofuran-5-yl}-1H-pyrrolo[2,3-b]pyridin-3-yl)ethyl]acetamide, N-[2-(5-{3-[2-(acetylamino)ethyl]-1H-indol-5-yl}-1H-pyrrolo[2,3-b]pyridin-3-yl)ethyl]acetamide, N-[2-(5-{3-[2-(acetylamino)ethyl]-1-benzothien-5-yl}-1H-pyrrolo[2,3-b]pyridin-3-yl)ethyl]acetamide.

The enantiomers, diastereoisomers and addition salts thereof with a pharmaceutically acceptable acid or base of the preferred compounds of the invention form an integral part of the invention.

The present invention relates also to a process for the preparation of compounds of formula (I), characterised in that there is used as starting material a compound of formula (V):

A—G$_1$—Cy—OMe  (V)

wherein A, G$_1$ and Cy are as defined for formula (I), which is subjected to demethylation using conventional agents, such as HBr, AlCl$_3$, AlBr$_3$, BBr$_3$ or Lewis acid/nucleophile binary systems, such as, for example, AlCl$_3$/PhCH$_2$SH or BBr$_3$/Me$_2$S, to obtain a compound of formula (VI):

A—G$_1$—Cy—OH  (VI)

wherein A, G$_1$ and Cy are as defined hereinbefore, which is converted, in conventional manner, by the action of, for example, sodium N,N-dimethylthiocarbamate, to the corresponding thiol of formula (VII):

A—G$_1$—Cy—SH  (VII)

wherein A, G$_1$ and Cy are as defined hereinbefore, or to the corresponding amine compound of formula (VIII):

A—G$_1$—Cy—NHR'$_a$  (VIII)

wherein A, G$_1$ and Cy are as defined hereinbefore and R'$_a$ can have any of the meanings of R$_a$ as defined for formula (I) and can also represent a hydrogen atom, which compounds of formulae (VI), (VII) and (VIII) represent the compound of formula (IX):

A—G$_1$—Cy—W$_4$H  (IX)

wherein W$_4$ represents an oxygen or sulphur atom, or an NH or NR$_a$ group (wherein R$_a$ is as defined hereinbefore), which compound of formula (IX) is condensed with:

a compound of formula (X):

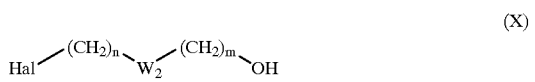

$$Hal{\sim}(CH_2)_n{\sim}W_2{\sim}(CH_2)_m{\sim}OH \quad (X)$$

wherein Hal represents a bromine, chlorine or iodine atom, and n, W$_2$ and m are as defined for formula (I), (with the proviso that it is not possible to have two consecutive hetero atoms and that the chain so defined may have one or more unsaturated bonds), or a compound of formula (XI):

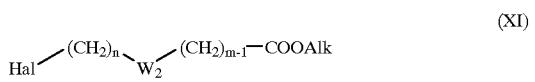

$$Hal{\sim}(CH_2)_n{\sim}W_2{\sim}(CH_2)_{m-1}{-}COOAlk \quad (XI)$$

wherein Hal, n, m and W$_2$ are as defined hereinbefore and Alk represents an alkyl radical (with the proviso that it is not possible to have two consecutive hetero atoms and that the chain so defined may have one or more unsaturated bonds), followed by reduction, to yield a compound of formula (XII):

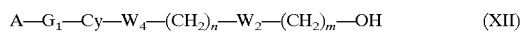

A—G$_1$—Cy—W$_4$—(CH$_2$)$_n$—W$_2$—(CH$_2$)$_m$—OH  (XII)

wherein A, G$_1$, Cy, W$_4$, n, m and W$_2$ are as defined hereinbefore (with the proviso that it is not possible to have two consecutive hetero atoms in the —W$_4$—

$(CH_2)_n-W_2-(CH_2)_m-OH$ chain and that the chain so defined may have one or more unsaturated bonds), the hydroxyl function of which is converted in conventional manner to a leaving group, such as, for example, a mesylate, a tosylate, or a halogen compound, to yield a compound of formula (XII'):

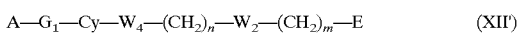  (XII')

wherein A, $G_1$, Cy, $W_4$, n, $W_2$ and m are as defined hereinbefore and E represents a mesyl or tosyl group or a halogen atom which is subjected to the action of a compound of formula (XIII):

  (XIII)

wherein B, $G_3$ and Cy' are as defined for formula (I) and $W'_4$ can have the same meanings as $W_4$ defined hereinbefore, to yield a compound of formula (I/a), a particular case of the compounds of formula (I):

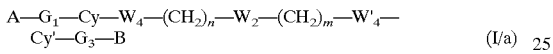  (I/a)

wherein A, $G_1$, Cy, Cy', $W_4$, n, $W_2$, m, $W'_4$, $G_3$ and B are as defined hereinbefore, or converted using, for example, phenyl bis(trifluoromethanesulphonimide) in a basic medium to the corresponding trifluoromethanesulphonate of formula (XIV)

  (XIV)

wherein A, $G_1$ and Cy are as defined hereinbefore, which is subjected, under conditions of catalysis by a suitable palladium compound, to the action of a boric acid compound $(R_bB(OH)2)$ or of a tin compound $(R_bSnBu3)$ (wherein $R_b$ represents a grouping of formula (XV):

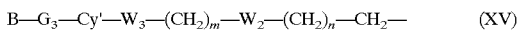  (XV)

wherein B, $G_3$, Cy', $W_3$, m, $W_2$ and n are as defined hereinbefore, with the proviso that it is not possible to have two consecutive hetero atoms in the $-W_3-(CH_2)_m-W_2-$ chain and that the chain so defined may have one or more unsaturated bonds), to yield a compound of formula (I/b), a particular case of the compounds of formula (I):

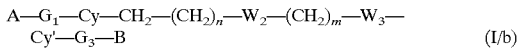  (I/b)

wherein A, $G_1$, Cy, Cy', n, $W_2$, m, $W_3$, $G_3$ and B are as defined hereinbefore (with the proviso that it is not possible to have two consecutive hetero atoms in the $-W_2-(CH_2)_m-W_3-$ chain and that the chain so defined may have one or more unsaturated bonds), which compounds of formula (I/c), a particular case of the compounds of formula (I):

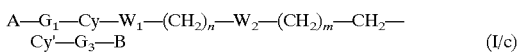  (I/c)

wherein A, $G_1$, Cy, Cy', $W_1$, n, $W_2$, m, $G_3$ and B are as defined hereinbefore (with the proviso that it is not possible to have two consecutive hetero atoms in the $-W_1-(CH_2)_n-W_2-$ chain and that the chain so defined may have one or more unsaturated bonds), are obtained according to a similar procedure starting from a compound of formula (XIV'):

  (XIV')

wherein B, $G_3$ and Cy' are as defined hereinbefore, or is treated, under coupling conditions using, for example, nickel or palladium compounds, with a compound of formula (XIV') to yield a compound of formula (I/d), a particular case of the compounds of formula (I):

  (I/d)

wherein A, $G_1$, Cy, Cy', $G_3$ and B are as defined hereinbefore, the totality of the compounds (I/a) to (I/d) constituting the compounds of formula (I) which may be purified, if desired, by a conventional purification technique, are separated, where appropriate, into their isomers according to a conventional separation technique, and converted, if necessary, into addition salts thereof with a pharmaceutically acceptable acid or base.

The compounds of formula (V) are readily accessible to the person skilled in the art according to methods described in the literature.

The compounds of the invention and the pharmaceutical compositions containing them have proved to be useful in the treatment of disorders of the melatoninergic system.

Pharmacological study of the compounds of the invention has in fact shown that they are atoxic, have a high affinity for melatonin receptors and have substantial activities in respect of the central nervous system and in respect of microcirculation, enabling it to be established that the compounds of the invention are useful in the treatment of stress, sleep disorders, anxiety, seasonal affective disorder, cardiovascular pathologies, pathologies of the digestive system, insomnia and fatigue due to jetlag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the compounds of the invention can be used in the treatment of sexual dysfunctions, that they have ovulation-inhibiting and immunomodulating properties and are capable of being used in the treatment of cancers.

The compounds will preferably be used in the treatment of seasonal affective disorder sleep disorders, cardiovascular pathologies, insomnia and fatigue due to jetlag, appetite disorders and obesity.

For example, the compounds will be used in the treatment of seasonal affective disorder and sleep disorders.

The present invention relates also to pharmaceutical compositions comprising at least one compound of formula (I) on its own or in combination with one or more pharmaceutically acceptable excipients.

Among the pharmaceutical compositions according to the invention, there may be mentioned more especially those that are suitable for oral, parenteral, nasal, per- or transcutaneous, rectal, perlingual, ocular or respiratory administration and especially tablets or dragees, sublingual tablets, sachets, paquets, gelatin capsules, glossettes, lozenges, suppositories, creams, ointments, dermal gels, and drinkable or injectable ampoules.

The dosage varies according to the sex, age and weight of the patient, the route of administration, the nature of the therapeutic indication or any associated treatments, and ranges from 0.01 mg to 1 g per 24 hours in one or more administrations.

The following Examples illustrate the invention but do not limit it in any way. The following Preparations yield compounds of the invention or synthesis intermediates for use in the preparation of the invention.

PREPARATION 1

N-[2-(7-Hydroxy-1-naphthyl)ethyl]-acetamide

Under an inert atmosphere, 27.5 mmol of the boron tribromide/dimethyl sulphide complex are dissolved in 100 ml of dichloromethane and stirred for 15 minutes at room temperature. A solution of 13.7 mmol of N-[2-(7-methoxy-1-naphthyl)ethyl]acetamide in 50 ml of dichloromethane is added, and the reaction mixture is refluxed for 30 hours. After cooling, the reaction mixture is hydrolysed cautiously and the dichloromethane is removed by evaporation. The mixture is then extracted with ethyl acetate, and the combined organic phases are washed with an aqueous 1M potassium hydrogen carbonate solution. The organic phase is dried over magnesium sulphate and concentrated to yield the title compound. White solid.

Melting point: 125–126° C.

Preparations 2 to 35 are obtained by proceeding as for Preparation 1 starting from the appropriate substrate:

PREPARATION 2

N-[2-(5-Hydroxy-1-benzofuran-3-yl)ethyl]acetamide

PREPARATION 3

N-[2-(5-Hydroxy-1-benzofuran-3-yl)ethyl] cyclopropanecarboxamide

PREPARATION 4

N-[2-(5-Hydroxy-1-benzofuran-3-yl)ethyl]-2-furamide

PREPARATION 5

N-[2-(7-Hydroxy-1-naphthyl)ethyl]benzamide

PREPARATION 6

N-[2-(7-Hydroxy-1-naphthyl)ethyl]-3-butenamide

PREPARATION 7

N-[2-(5-Hydroxy-1-benzofuran-3-yl)ethyl]-2-methylpropanamide

PREPARATION 8

N-[2-(7-Hydroxy-1-naphthyl)ethyl]-2-phenylacetamide

PREPARATION 9

N-[2-(5-Hydroxy-1-benzothiophen-3-yl)ethyl] acetamide

PREPARATION 10

N-[2-(5-Hydroxy-1H-pyrrolo[2,3-b]pyridin-3-yl) ethyl]-cyclopropanecarboxamide

PREPARATION 11

N-[2-(5-Hydroxy-1H-indol-3-yl)ethyl]acetamide

PREPARATION 12

N-[2-(5-Hydroxy-1H-pyrrolo[2,3-b]pyridin-3-yl) ethyl]acetamide

PREPARATION 13

N-[2-(7-Hydroxy-1-naphthyl)ethyl] cyclobutanecarboxamide

PREPARATION 14

2,2,2-Trifluoro-N-[2-(7-hydroxy-1-naphthyl)ethyl] acetamide

PREPARATION 15

N-[(6-Hydroxy-2H-chromen-3-yl)methyl] butanamide

PREPARATION 16

N-[(6-Hydroxy-2H-chromen-3-yl)methyl]acetamide

PREPARATION 17

N-[(7-Hydroxy-1,4-benzodioxin-2-yl)methyl]-N'propylurea

PREPARATION 18

N-[(7-Hydroxy-1,4-benzodioxin-2-yl)methyl] acetamide

PREPARATION 19

N-[2-(7-Hydroxy-1-naphthyl)ethyl]furamide

PREPARATION 20

N-[2-(2-Benzyl-5-hydroxy-1H-pyrrolo[2,3-b] pyridin-3-yl)ethyl]acetamide

PREPARATION 21

N-[2-(5-Hydroxy-1-benzothiophen-3-yl)ethyl]
cyclohexane-carboxamide

PREPARATION 22

N-Hexyl-2-(5-hydroxy-1-benzofuran-3-yl)acetamide

PREPARATION 23

2,2,2-Trifluoro-N-[2-(5-hydroxy-1-benzothiophen-3-yl)ethyl]-acetamide

PREPARATION 24

N-[2-(6-Hydroxy-3,4-dihydro-2H-chromen-4-yl)ethyl]acetamide

PREPARATION 25

N-[2-(7-Hydroxy-1,2,3,4-tetrahydro-1-naphthalenyl)ethyl]-acetamide

PREPARATION 26

N-[2-(7-Hydroxy-1,2,3,4-tetrahydro-1-naphthalenyl)ethyl]-cyclopropanecarboxamide

PREPARATION 27

N-[2-(7-Hydroxy-1-naphthyl)ethyl]heptanamide

PREPARATION 28

N-[2-(5-Hydroxy-1H-indol-3-yl)ethyl]
cyclobutanecarboxamide

PREPARATION 29

4-(7-Hydroxy-1-naphthyl)-N-isopropylbutanamide

PREPARATION 30

N-[2-(5-Hydroxy-1-benzofuran-3-yl)ethyl]-N'-phenylurea

PREPARATION 31

N-Benzyl-2-(5-hydroxy-1-benzothiophen-3-yl)acetamide

PREPARATION 32

N-[2-(5-Hydroxy-1H-inden-3-yl)ethyl]pentanamide

PREPARATION 33

3-(5-Hydroxy-1-benzofuran-3-yl)-N-methylpropanamide

PREPARATION 34

N-[2-(5-Hydroxy-1H-pyrrolo[2,3-b]pyridin-3-yl)ethyl]-N'-methylurea

PREPARATION 35

4-(5-Hydroxy-1H-indol-3-yl)-N-methylbutanamide

PREPARATION 36

N-[2-(5-Mercapto-1-benzofuran-3-yl)ethyl]
acetamide

The product obtained in Step A (9 mmol) is added, with stirring, to a solution of potassium hydroxide (10 mmol) dissolved in 15 ml of water and 16 ml of tetrahydrofuran. The solution is cooled using a bath of ice and salt, and dimethylthiocarbamoyl chloride (9 mmol) dissolved in tetrahydrofuran (15 ml) is added dropwise with stirring. After stirring for half an hour while maintaining the cold temperature, the reaction mixture is extracted with chloroform. The organic phases are combined, dried over magnesium sulphate, filtered and then concentrated under reduced pressure. The residue is taken up in diphenyl ether (10 ml) and refluxed for one hour under a nitrogen atmosphere. The diphenyl ether is removed by evaporation under reduced pressure until a solution of about 2 ml has been obtained. The 2 ml of distillate, which are still hot, are poured carefully into 50 ml of hexane to yield, after cooling, a solid which is isolated by filtration. The solid collected in that manner is added to a solution of potassium hydroxide (380 mg) dissolved in a water/methanol mixture (1 ml/10 ml). The solution is refluxed for 12 hours and then cooled and concentrated under reduced pressure. The residue is taken up in 20 ml of chloroform and extracted 3 times with water. The organic phase is dried over magnesium sulphate, filtered and concentrated under reduced pressure. The residue is chromatographed over silica gel to yield the title product.

PREPARATION 37

N-[2-(5-Mercapto-1-benzothiophen-3-yl)ethyl]
butanamide

Step A: N-[2-(5-Hydroxy-1-benzothiophen-3-yl)ethyl]butanamide

The procedure is as for Preparation 1 starting from N-[2-(5-methoxy-1-benzothiophen-3-yl)ethyl]butanamide.

Step B: N-[2-(5-Mercapto-1-benzothiophen-3-yl)ethyl]butanamide

The procedure is as for Preparation 36 starting from the compound obtained in Step A.

PREPARATION 38

N-[2-{5-Mercapto-2-[4-(trifluoromethyl)benzyl]-1-benzothiophen-3-yl}ethyl)acetamide Step A : N-(2-{5-Hydroxy-2-[4-(trifluoromethyl)benzyl]-1-benzothiophen-3-yl}ethyl)acetamide The procedure is as for Preparation 1 starting from N-(2-{5-methoxy-2-[4-(trifluoromethyl)benzyl]-1-benzothiophen-3-yl}ethyl)acetamide.

Step B: N-(2-{5-Mercapto-2-[4-(trifluoromethyl)benzyl]-1-benzothiophen-3-yl}ethyl)acetamide The procedure is as for Preparation 36 starting from the compound obtained in Step A.

PREPARATION 39

N-[2-(7-Mercapto-1,2,3,4-tetrahydro-1-naphthalenyl)ethyl]-cyclopropanecarboxamide The procedure is as for Preparation 36 starting from the compound obtained in Preparation 26.

PREPARATION 40

N-[2-(5-Amino-1-benzofuran-3-yl)ethyl]acetamide

Step A: N-[2-(5-Bromo-1-benzofuran-3-yl)ethyl]acetamide

Triphenylphosphine (10 mmol) and acetonitrile (70 ml) are poured into a 150 ml three-necked flask equipped with a dropping funnel, a cooler on top of which is mounted a tube filled with calcium chloride, and a mechanical stirrer. The solution is cooled using an ice-bath while maintaining stirring, and bromine (10 mmol) is added. When the addition is complete, the ice-bath is withdrawn and then the product obtained in Preparation 2 (8 mmol) is added. The reaction mixture is stirred at 60–70° C. until the starting material has disappeared. At the end of the reaction, the mixture is filtered, and then the filtrate is concentrated under reduced pressure. The residue is taken up in ethyl acetate, washed with water and then with a saturated potassium hydrogen carbonate solution, and once again with water, and then dried over magnesium sulphate and concentrated under reduced pressure. The residue is filtered over silica gel to yield the title product.

Step B: N-[2-(5-Iodo-1-benzofuran-3-yl)ethyl]acetamide

A mixture of the product obtained in Step A (2 mmol), potassium iodide (30 mmol) and copper(I) iodide (10 mmol) in hexamethylphosphoramide (6 ml) is heated at 150–160° C. with stirring under a nitrogen atmosphere until a 90% conversion rate has been reached. Dilute hydrochloric acid is then added, followed by ether, and the mixture is then filtered to remove the insoluble copper(I) salts. The organic phase is separated off, washed with a solution of sodium sulphite and with water, dried over magnesium sulphate and evaporated to yield a residue which is chromatographed over silica gel to yield the title product.

Step C: N-[2-(5-Vinyl-1-benzofuran-3-yl)ethyl]acetamide 15 mmol of the product obtained in Step B, 16 mmol of vinyl tributyltin and 0.43 mmol of tetrakis(triphenylphosphine)palladium, are heated at 110° C., with stirring, for 3 hours in 30 ml of N-methylpyrrolidinone. After removal of the solvent by evaporation, the residue is taken up in 20 ml of dichloromethane and treated with an aqueous 10% potassium fluoride solution. Extraction, concentration under reduced pressure and chromatography over silica gel yield the pure title product.

Step D: N-[2-(5-Formyl-1-benzofuran-3-yl)ethyl]acetamide 1.10 g of osmium tetroxide in 2-methyl-2-propanol and then 8.70 g of sodium periodate are added at room temperature to a solution of 10 mmol of the product obtained in Step C in a mixture of 50 ml of dioxane and 25 ml of water. After stirring overnight at room temperature, the suspension is filtered and the filtrate is concentrated under reduced pressure. The resulting residue is taken up in dichloromethane. The organic phase is washed with water, dried and evaporated. The residue is purified by chromatography over silica gel to yield the title product.

Step E: 3-[2-(Acetylamino)ethyl]-1-benzofuran-5-carboxylic acid 2.7 g of potassium permanganate in 50 ml of an acetone/water mixture (50/50) are added at room temperature to a solution of 6.88 mmol of the product obtained in Step D in 30 ml of acetone. The solution is stirred for 2 hours at room temperature and then filtered. The filtrate is concentrated under reduced pressure and chromatographed over silica gel to yield the title product.

Step F: 3-[2-(Acetylamino)ethyl]-1-benzofuran-5-carboxylic acid chloride 5 mmol of the product obtained in Step E are dissolved in 40 ml of thionyl chloride. After stirring under an inert atmosphere for 1 hour, the thionyl chloride is removed by evaporation under reduced pressure to yield the title product.

Step G: N-[2-(5-Amino-1-benzofuran-3-yl)ethyl]acetamide

A solution of the product obtained in Step F (20 mmol) in dichloromethane (30 ml) containing tetrabutylammonium bromide (20 mg) is cooled in an ice-bath. After the addition of sodium azide (25 mmol) dissolved in 5 ml of water, the solution is stirred vigorously at 0° C. for 2 hours. The organic phase is separated off, washed with water (2×5 ml) and dried over magnesium sulphate. After filtration, trifluoroacetic acid (30 mmol) is added and the solution is stirred under reflux for 60 hours. After cooling, the organic phase is washed with a saturated sodium hydrogen carbonate solution (2×5 ml) and concentrated under reduced pressure. The residue is then taken up in methanol (20 ml), and water (80 ml) and then potassium carbonate (30 mmol) are added. After stirring at room temperature for 20 hours, the reaction mixture is concentrated under reduced pressure to a volume of about 60 ml, and is then extracted 3 times with ether (3×50 ml). After drying over sodium sulphate, the organic phase is filtered and then evaporated under reduced pressure. The residue is chromatographed over silica gel to yield the title product.

PREPARATION 41

N-[2-(5-Amino-1-benzothiophen-3-yl)ethyl]pentanamide

Step A: N-[2-(5-Hydroxy-1-benzothiophen-3-yl)ethyl]pentanamide

The procedure is as for Preparation 1 starting from N-[2-(5-methoxy-1-benzothiophen-3-yl)ethyl]pentanamide.

Step B: N-[2-(5-Amino-1-benzothiophen-3-yl)ethyl]pentanamide

The procedure is as for Preparation 40 starting from the compound obtained in Step A.

PREPARATION 42

N-{2-[5-Amino-2-(3-methoxybenzyl)-1-benzofuran-3-yl]ethyl}-acetamide

Step A: N-{2-[5-Hydroxy-2-(3-methoxybenyl)-1-benzofuran-3-yl]ethyl}-acetamide

The procedure is as for Preparation 1 starting from N-{2-[5-methoxy-2-(3-methoxy-benzyl)-1-benzofuran-3-yl]ethyl}acetamide.

Step B: N-{2-[5-Amino-2-(3-methoxybenzyl)-1-benzofuan-3-yl]ethyl}-acetamide

The procedure is as for Preparation 40 starting from the compound obtained in Step A.

PREPARATION 43

N-[2-(5-Amino-1-benzofuran-3-yl)ethyl]-2-furamide

The procedure is as for Preparation 40 starting from the compound obtained in Preparation 4.

PREPARATION 44

N-[2-(5-Amino-1-benzofuran-3-yl)ethyl]-N'-cyclopropylurea

Step A: N-[2-(5-Hydroxy-1-benzofuran-3-yl)ethyl]-N'-cyclopropylurea

The procedure is as for Preparation 1 starting from N-[2-(5-methoxy-1-benzofuran-3-yl)ethyl]-N'-cyclopropylurea Step B: N-[2-(5-Amino-1-benzofuran-3-yl)ethyl]-N'-cyclopropylurea The procedure is as for Preparation 40 starting from the compound obtained in Step A.

PREPARATION 45

3-[2-(Acetylamino)ethyl]-1-benzofuran-5-yl trifluoromethane-sulphonate 60 ml of triethylamine are added to a solution of 0.07 mol of the compound obtained in Preparation 2 in one liter of dichloromethane. The reaction mixture is refluxed until dissolution, and then 0.1 mol of phenyl bis(trifluoromethanesulphonimide) and 0.75 mol of potassium carbonate are added. After refluxing for 4 hours, the mixture is washed with one liter of 1M sodium hydrogen carbonate and then with one liter of 1M hydrochloric acid. The organic phase is dried, concentrated and purified by chromatography over silica gel to yield the title product.

Preparations 46 to 70 are obtained by proceeding as for Preparation 45.

PREPARATION 46

8-[2-(Acetylamino)ethyl]-2-naphthyl trifluoromethanesulphonate

Starting material: Preparation 1

PREPARATION 47

3-{2-[(Cyclopropylcarbonyl)amino]ethyl}-1-benzothiophen-5-yl trifluoromethanesulphonate Starting material: N-[2-(5-Hydroxy-1-benzothiophen-3-yl)ethyl]cyclopropanecarboxamide, obtained by proceeding as for Preparation 1 starting from N-[2-(5-methoxy-1-benzothiophen-3-yl)ethyl]cyclopropanecarboxamide.

PREPARATION 48

8-(2-{[(Methylamino)carbonyl]amino}ethyl)-2-naphthyl trifluoromethanesulphonate

Starting material: N-[2-(7-Hydroxy-1-naphthyl)ethyl]-N'-methylurea obtained by proceeding as for Preparation 1 starting from N-[2-(7-methoxy-1-naphthyl)ethyl]-N'-methylurea.

PREPARATION 49

3-{2-1(Anilinocarbonyl)amino]ethyl}-1-benzofuran-5-yl trifluoromethanesulphonate Starting material: Preparation 30

PREPARATION 50

3-[2-(2-Furoylamino)ethyl]-1-benzothiophen-5-yl trifluoromethanesulphonate

Starting material: N-[2-(5-Hydroxy-1-benzothiophen-3-yl)ethyl]-2-furamide, obtained by proceeding as for Preparation 1 starting from N-[2-(5-methoxy-1-benzothiophen-3-yl)ethyl]-2-furamide.

PREPARATION 51

3-[2-(Benzylamino)-2-oxoethyl]-1H-indol-5-yl trifluoromethanesulphonate

Starting material: N-Benzyl-2-(5-hydroxy-]H-indol-3-yl) acetamide, obtained by proceeding as for Preparation 1 starting from N-benzyl-2-(5-methoxy-1H-indol-3-yl) acetamide.

PREPARATION 52

3-[3-(Benzoylamino)propyl]-1H-indol-5-yl trifluoromethanesulphonate

Starting material: N-[3-(5-Hydroxy-1H-indol-3-yl)propyl]benzamide, obtained by proceeding as for Preparation 1 starting from N-[3-(5-methoxy-1H-indol-3-yl)propyl]benzamide.

PREPARATION 53

3-[2-(Isobutyrylamino)ethyl)-1-benzothiophen-5-yl trifluoromethanesulphonate

Starting material N-[2-(5-Hydroxy-1-benzothiophen-3-yl)ethyl]-2-methylpropanamide, obtained by proceeding as for Preparation 1 starting from N-[2-(5-methoxy-1-benzothiophen-3-yl)ethyl]-2-methylpropanamide.

PREPARATION 54

3-[2-(Heptanoylamino)ethyl]-1H-pyrrolo[2,3-b]pyridin-5-yl trifluoromethanesulphonate Starting material: N-[2-(5-Hydroxy-1H-pyrrolo[2, 3-b]pyridin-3-yl)ethyl]heptanamide. obtained by proceeding as for Preparation 1 starting from N-[2-(5-methoxy-1H-pyrrolo[2,3-b]pyridin-3-yl)ethyl]heptanamide.

PREPARATION 55

3-[2-(Acetylamino)ethyl]-1H-pyrrolo[2,3-b]pyridin-5-yl trifluoromethanesulphonate Starting material: Preparation 12

PREPARATION 56

3-[4-(Cyclopentylamino)-4-oxobutyl]-1-benzofuran-5-yl trifluoromethanesulphonate Starting material: N-Cyclopentyl-4-(5-hydroxy-1-benzofuran-3-yl)butanamide, obtained by proceeding as for Preparation 1 starting from N-cyclopentyl-4-(5-methoxy-1-benzofuran-3-yl)butanamide.

PREPARATION 57

3-{2-[(Cyclopropylcarbonyl)amino]ethyl}-1H-pyrrolo-[2,3-b]-pyridin-5-yl trifluoromethanesulphonate Starting material: Preparation 10

PREPARATION 58

3-(2-{[(Allylamino)carbonyl]amino}ethyl)-1-benzothiophen-5-yl trifluoromethanesulphonate Starting material: N-Allyl-N'-[2-(5-hydroxy-1-benzothiophen-3-yl)ethyl]urea, obtained by proceeding as for Preparation 1 starting from N-allyl-N'-[2-(5-methoxy-1-benzothiophen-3-yl)ethyl]urea.

PREPARATION 59

3-[(Acetylamino)ethyl]-1,4-benzodioxin-6-yl trifluoromethanesulphonate

Starting material: Preparation 18

PREPARATION 60

3-[2-(Isobutyrylamino)ethyl]-1-benzofuran-5-yl trifluoromethanesulphonate

Starting material: Preparation 7

PREPARATION 61

4-{2-[(2,2,2-Trifluoroacetyl)amino]ethyl}-3,4-dihydro-2H-chromen-6-yl trifluoromethanesulphonate Starting material: 2,2,2-Trifluoro-N-[2-(6-hydroxy-3,4-dihydro-2H-chromen-4-yl)ethyl]acetamide, obtained by proceeding as for Preparation 1 starting from 2,2,2-trifluoro-N-[2-(6-methoxy-3,4-dihydro-2H-chromen-4-yl)ethyl]acetamide.

PREPARATION 62

3-(4-Anilino-4-oxobutyl)-1-benzothiophen-5-yl trifluoromethanesulphonate

Starting material: 4-(5-Hydroxy-1-benzothiophen-3-yl)-N-phenylbutanamide, obtained by proceeding as for Preparation 1 starting from 4-(5-methoxy-1-benzothiophen-3-yl)-N-phenylbutanamide.

PREPARATION 63

3-[(Acetylamino)methyl]-3,4-dihydro-2H-chromen-6-yl trifluoromethanesulphonate Starting material: N-[(6-Hydroxy-3,4-dihydro-2H-chromen-3-yl)methyl]acetamide, obtained by proceeding as for Preparation 1 starting from N-[(6-methoxy-3,4-dihydro-2H-chromen-3-yl)methyl]acetamide.

PREPARATION 64

3-[2-(Acetylamino)ethyl]-2-[4-(trifluoromethyl)benzyl]-1-benzofuran-5-yl trifluoromethanesulphonate Starting material: N-(2-{5-Hydroxy-2-[4-(trifluoromethyl)benzyl]-1-benzofuran-3-yl}-ethyl)acetamide, obtained by proceeding as for Preparation 1 starting from N-(2-{5-methoxy-2-[4-(trifluoromethyl)benzyl]-1-benzofuran-3-yl}ethyl)acetamide.

PREPARATION 65

3-(2-{[(Methylamino)carbonyl]amino}ethyl)-1H-indol-5-yl trifluoromethanesulphonate Starting material: N-[2-(5-Hydroxy-1H-indol-3-yl)ethyl]-N'-methylurea, obtained by proceeding as for Preparation 1 starting from N-[2-(5-methoxy-1H-indol-3-yl)ethyl]-N'-methylurea.

PREPARATION 66

4-{2-[(2,2-Dimethylpropanoyl)amino]ethyl}-3,4-dihydro-2H-chromen-6-yl trifluoromethanesulphonate Starting material: N-[2-(6-Hydroxy-3,4-dihydro-2H-chromen-4-yl)ethyl]-2,2-dimethyl-propanamide, obtained by proceeding as for Preparation 1 starting from N-[2-(6-methoxy-3,4-dihydro-2H-chromen-4-yl)ethyl]-2,2-dimethylpropanamide.

PREPARATION 67

3-[2-(Acetylamino)ethyl]-1H-indol-5-yl trifluoromethanesulphonate

Starting material: N-acetylserotonin.

PREPARATION 68

3-{[(Cyclohexylcarbonyl)amino]methyl}-1,4-benzodioxin-6-yl trifluoromethanesulphonate Starting material: N-[(7-Hydroxy-1,4-benzodioxin-2-yl)methyl]cyclohexanecarboxamide, obtained by proceeding as for Preparation 1 starting from N-[(7-methoxy-1,4-benzodioxin-2-yl)methyl]cyclohexanecarboxamide.

PREPARATION 69

3-[2-(Acetylamino)ethyl]-2-(3-methoxybenzyl)-1-benzothiophen-5-yl trifluoromethanesulphonate Starting material: N-{2-[5-Hydroxy-2-(3-methoxybenzyl)-1-benzothiophen-3-yl]ethyl}-acetamide, obtained by proceeding as for Preparation 1 starting from N-{2-[5-methoxy-2-(3-methoxybenzyl)-1-benzothiophen-3-yl]-ethyl}acetamide.

PREPARATION 70

3-[3-(Acetylamino)propyl]-1-benzofuran-5-yl trifluoromethanesulphonate

Starting material N-[3-(5-Hydroxy-1-benzofuran-3-yl)propyl]acetamide, obtained by proceeding as for Preparation 1 starting from N-[3-(5-methoxy-1-benzofuran-3-yl)propyl]acetamide.

PREPARATION 71

N-{2-[5-Hydroxy-1-(phenylsulphonyl)-1H-indol-3-yl]ethyl}-acetamide

Step A: N-{2-[5-Methoxy-1-(phenylsulphonyl)-1H-indol-3-yl]ethyl}acetamide 5 g of melatonin are dissolved in 150 ml of dichloromethane, and then 3.41 g of sodium hydroxide and 0.35 g of tetrabutylammonium hydrogen sulphate are added. The reaction mixture is then cooled in an ice-bath, and 4.06 ml of benzenesulphonyl chloride are added dropwise. After stirring overnight at room temperature, the excess sodium hydroxide and the catalyst are filtered off, the solvent is removed by evaporation in vacuo, and the resulting solid is recrystallised to yield the title product in the form of white crystals.

Melting point: 140–141° C.

Step B: N-{2-[5-Hydroxy-1-(phenylsulphonyl)-1H-indol-3-yl]ethyl}acetamide 5 g of the compound obtained in Step A are dissolved in 100 ml of dichloromethane. The reaction mixture is then cooled in an ice-bath, and 3.81 ml of boron tribromide are added dropwise. After stirring at room temperature for two hours, the reaction mixture is poured into 500 ml of water and ice. The precipitate that forms is filtered off, washed with water and oven-dried at 50° C.

Melting point : 205–206° C.

PREPARATION 72

3-[2-(Acetylamino)ethyl]-1-benzothien-5-yl trifluoromethanesulphonate

The procedure is as for Preparation 45 starting from the compound obtained in Preparation 9.

EXAMPLE 1

N-(2-{7-[2-({3-[2-(Acetylamino)ethyl]-1-benzofuran-5-yl}oxy)ethoxy]-1-naphthyl}ethyl)acetamide Step A: N-{2-[7-(2-Bromoethoxy)naphth-1-yl]ethyl}acetamide The compound obtained in Preparation 1 (0.009 mol) is dissolved in 20 ml of a mixture of dimethyl sulphoxide (6 ml) and butanone (14 ml). 0.027 mol of potassium carbonate and 0.036 mol of dibromoethane are added, and the mixture is heated at reflux for 48 hours. The reaction mixture is then cooled and poured into water. The aqueous phase is extracted with $Et_2O$, and then the organic phase is washed with water until the washing waters are neutral, and subsequently dried over magnesium sulphate and evaporated under reduced pressure. The resulting residue is purified by chromatography over silica gel (eluant acetone/cyclohexane (2/8)) and recrystallised. White solid.

Melting point: 110–111° C.

Elemental microanalysis:

| % | C | H | N |
|---|---|---|---|
| Calculated: | 57.15 | 5.40 | 4.17 |
| Found: | 57.28 | 5.38 | 3.91 |

Step B: N-(2-{7-[2-({3-[2-(Acetylamino)ethyl]-1-benzofuran-5-yl}oxy)ethoxy]-1-naphthyl}ethyl)acetamide In a 100 ml round-bottomed flask, 0.003 mol of the compound obtained in Preparation 2 and 0.003 mol of the compound obtained in Step A are dissolved in a mixture of 3 ml of dimethyl sulphoxide and 20 ml of butanone. 0.009 mol of potassium carbonate and one potassium iodide crystal are added and then the mixture is heated at reflux for 12 hours. The reaction mixture is then cooled and poured into 100 ml of water. The precipitate that forms is suctioned off and recrystallised.

EXAMPLE 2

N-(2-1{5-[2-({8-[2-(Acetylamino)ethyl]-2-naphthyl}oxy)ethoxy]-1-benzofuran-3-yl}ethyl)cyclopropanecarboxamide The procedure is as for Example 1, in Step B replacing the compound obtained in Preparation 2 by the compound obtained in Preparation 3.

EXAMPLE 3

N-(2-{5-[2-({8-[2-(Acetylamino)ethyl]-2-naphthyl}oxy)ethoxy]-1-benzofuran-3-yl}ethyl)-2-furamide The procedure is as for Example 1, in Step B replacing the compound obtained in Preparation 2 by the compound obtained in Preparation 4.

EXAMPLE 4

N-(2-{7-[2-({3-[2-(Acetylamino)ethyl]-1-benzofuran-5-yl}thio)ethoxy]-1-naphthyl}ethyl)benzamide The procedure is as for Example 1, replacing:

in Step A, the compound obtained in Preparation 1 by the compound obtained in Preparation 5, in Step B, the compound obtained in Preparation 2 by the compound obtained in Preparation 36.

EXAMPLE 5

N-(2-{7-[2-({3-[2-(Acetylamino)ethyl]-1-benzofuran-5-yl}amino)-ethoxy]-1-naphthyl}ethyl)acetamide The procedure is as for Example 1, in Step B replacing the compound obtained in Preparation 2 by the compound obtained in Preparation 40.

EXAMPLE 6

N-(2-{7-[2-({3-[2-(Isobutyrylamino)ethyl]-1-benzofuran-5-yl}oxy)-ethoxyl]-1-naphthyl}ethyl)-3-butenamide The procedure is as for Example 1, replacing:

in Step A, the compound obtained in Preparation 1 by the compound obtained in Preparation 6, in Step B, the compound obtained in Preparation 2 by the compound obtained in Preparation 7.

EXAMPLE 7

N-(2-{7-[2-({3-[2-(Acetylamino)ethyl]-1-benzothiophen-5-yl}oxy)-ethoxy]-1-naphthyl}ethyl)-2-phenylacetamide The procedure is as for Example 1, replacing:
in Step A, the compound obtained in Preparation 1 by the compound obtained in Preparation 5,
in Step B, the compound obtained in Preparation 2 by the compound obtained in Preparation 9.

EXAMPLE 8

N-(2-{5-[2-({8-[2-(Acetylamino)ethyl]-2-naphthyl}oxy)ethoxy]-1H-pyrrolo[2,3-b]pyridin-3-yl}ethyl)cyclopropanecarboxamide The procedure is as for Example 1, in Step B replacing the product obtained in Preparation 2 by the compound obtained in Preparation 10.

EXAMPLE 9

N-(2-{5-[2-({3-[2-(Acetylamino)ethyl]-3a,7a-dihydro-1-benzofuran-5-yl}oxy)ethoxy]-1-benzothiophen-3-yl}ethyl)acetamide The procedure is as for Example 1, replacing:
in Step A, the compound obtained in Preparation 1 by the compound obtained in Preparation 2,
in Step B, the compound obtained in Preparation 2 by the compound obtained in Preparation 9.

EXAMPLE 10

N-(2-{5-[2-({3-[2-(Acetylamino)ethyl]-1H-indol-5-yl}oxy)ethoxy]-3a,b 7a-dihydro-1-benzofuran-3-yl ethyl}-2-furamide The procedure is as for Example 1, replacing:
in Step A, the compound obtained in Preparation 1 by the compound obtained in Preparation 4,
in Step B, the compound obtained in Preparation 2 by the compound obtained in Preparation 11.

EXAMPLE 11

N-(2-{5-[2-({3-[2-(Acetylamino)ethyl]-1H-pyrrolo[2,3-b]pyridin-5-yl}oxy)ethoxy]-3a,7a-dihydro-1-benzofuran-3-yl}ethyl)-2-methylpropanamide The procedure is as for Example 1, replacing:
in Step A, the compound obtained in Preparation 1 by the compound obtained in Preparation 7,
in Step B, the compound obtained in Preparation 2 by the compound obtained in Preparation 12.

EXAMPLE 12

N-(2-{7-[3-({3-[2-(Acetylamino)ethyl]-1-benzothiophen-5-yl}oxy)-propoxy]-1-naphthyl}ethyl)acetamide Step A N-{2-[7-(3-Hydroxypropyloxy)naphth-1-yl]ethyl}acetamide In a 100 ml round-bottomed flask, 0.022 mol of the compound obtained in Preparation 1 is dissolved in 30 ml of dimethylformamide. 0.066 mol of potassium carbonate and 0.033 mol of 3-bromopropan-1-ol are added, and then the mixture is heated at 80° C. for 4 hours. The reaction mixture is cooled and poured into 100 ml of a 1M HCl solution. The aqueous phase is extracted 3 times with Et₂O and then the organic phase is dried over MgSO₄ and evaporated under reduced pressure. The title product is obtained by recrystallisation. White solid.

Melting point: 141–142° C.

Step B:. 3-({8-[2-(Acetylamino)ethyl]-2-naphthyl}oxy)propyl methanesulphonate

In a 250 ml round-bottomed flask, the alcohol obtained in Step A is dissolved in 50 ml of dichloromethane, and 0.012 mol of triethylamine is added. The mixture is cooled in an ice/salt bath at –10° C., and then 0.012 mol of mesyl chloride is added dropwise with stirring with a magnetic stirrer. The reaction mixture is stirred at room temperature for 4 hours. 100 ml of water are then added, followed by extraction with CH₂Cl₂. The organic phase is washed with water, dried over MgSO₄ and evaporated under reduced pressure. The resulting oil is purified by chromatography over silica gel (eluant: acetone/cyclohexane (2/8)).

Step C: N-(2-{7-[3-({3-[2-(Acetylamino)ethyl]-1-benzothiophen-5-yl}oxy)-propoxy]-1-naphthy}ethyl)acetamide In a 100 ml round-bottomed flask containing 30 ml of methanol, 0.06 g of sodium is added in small portions. When the sodium has been completely used up, 0.0033 mol of the compound obtained in Preparation 9 is added, and the mixture is stirred for 20 minutes. The methanol is removed by evaporation under reduced pressure, the residue is taken up in 15 ml of DMF, and then 0.0027 mol of the compound obtained in Step B is added. The reaction mixture is then heated at reflux for 12 hours and subsequently cooled and poured into 100 ml of water and 10 ml of 3M HCl. After extraction with ethyl acetate, the organic phase is washed with a 10% sodium hydroxide solution and then with water. After drying over MgSO₄ and removal of the solvent by evaporation under reduced pressure, the title compound is purified by chromatography over silica gel.

EXAMPLE 13

N-(2-{7-[3-({3-[2-(Butyrylamino)ethyl]-1-benzothiophen-5-yl}thio)-propoxy]-1-naphthyl}ethyl)cyclobutanecarboxamide The procedure is as for Example 12, replacing:
in Step A, the compound obtained in Preparation 1 by the compound obtained in Preparation 13,
in Step C, the compound obtained in Preparation 9 by the compound obtained in Preparation 37.

EXAMPLE 14

N-{2-[5-({3-[(8-{2-[(2,2,2-Trifluoroacetyl)amino]ethyl}-2-naphthyl)oxy]propyl}amino)-1-benzothiophen-3-yl]-ethyl}pentanamide The procedure is as for Example 12, replacing:
in Step A, the compound obtained in Preparation 1 by the compound obtained in Preparation 14,
in Step C, the compound obtained in Preparation 9 by the compound obtained in Preparation 41.

EXAMPLE 15

N-({6-[3-({8-[2-(Acetylamino)ethyl]-2-naphthyl}oxy)propoxy]-2H-chromen-3-yl}methyl)butanamide The procedure is as for Example 12, in Step C replacing the compound of Preparation 9 by the compound of Preparation 15.

EXAMPLE 16

N-(2-{5-[3-({3-[(Acetylamino)methyl]-2H-chromen-6-yl}oxy)propoxy]-1-benzofuran-3-yl}ethyl)cyclopropanecarboxamide The procedure is as for Example 12, replacing:
in Step A, the compound of Preparation 1 by the compound of Preparation 16,
in Step C, the compound of Preparation 9 by the compound of Preparation 3.

EXAMPLE 17

N-{2-[5-(3-{[3-({[(Propylamino)carbonyl]amino}methyl)-1,4-benzodioxin-6-yl]oxy}propoxy)-1H-pyrrolo[2,3-b]pyridin-3-yl]ethyl}-acetamide The procedure is as for Example 12, replacing:
in Step A, the compound of Preparation 1 by the compound of Preparation 17,
in Step C, the compound of Preparation 9 by the compound of Preparation 12.

EXAMPLE 18

N-({7-[4-({8-[2-(Acetylamino)ethyl]-2-naphthyl}oxy)butoxy]-1,4-benzodioxin-2-yl}methyl)acetamide Step A: Ethyl 4-({8-[2-(acetylamino)ethyl]-2-naphthyl}oxy)butanoate In a 100 ml round-bottomed flask, 0.022 mol of the compound obtained in Preparation 1 is dissolved in 50 ml of acetonitrile. 0.066 mol of potassium carbonate is added, and the reaction mixture is stirred at 80° C. for 30 minutes. 0.033 mol of ethyl 1-bromobutyrate are then added dropwise and the reaction mixture is stirred for 1 hour at 80° C. The acetonitrile is removed by evaporation under reduced pressure, and the residue is dissolved in a 1N HCl solution. After extraction with ethyl acetate, washing of the organic phase with water, drying over $MgSO_4$ and evaporation under reduced pressure, the title compound is purified by recrystallisation. Beige solid.

Melting point: 64–66° C.

Step B: N-{2-[7-(4-Hydroxybutyloxy)naphth-1-yl]ethyl}acetamide

In a 250 ml round-bottomed flask, the ester obtained in Step A (0.009 mol) is dissolved in 100 ml of anhydrous ether. 0.009 mol of lithium aluminum hydride is added in portions, and the reaction mixture is stirred for 6 hours at room temperature. The reaction mixture is then hydrolysed with a few drops of 1M NaOH, and the precipitate that forms is filtered off. The filtrate is dried over $MgSO_4$ and evaporated under reduced pressure. The resulting residue is precipitated from an $Et_2O$/petroleum ether mixture (1/1), suctioned off and recrystallised. White solid.

Melting point: 82–84° C.

Elemental microanalysis:

| % | C | H | N |
|---|---|---|---|
| Calculated: | 71.73 | 7.69 | 4.64 |
| Found: | 72.00 | 7.58 | 4.45 |

Step C: 4-({8-[2-(Acetylamino)ethyl]-2-naphthyl}oxy)butyl methanesulphonate

The procedure is as for Step B of Example 12 starting from the compound obtained in Step B.

Step D: N-({7-[4-({8-[2-(Acetylamino)ethyl]-2-naphthyl}oxy)butoxy]-1,4-benzodioxin-2-yl}methyl)acetamide The procedure is as for Step C of Example 12, replacing the compound obtained in Preparation 9 by the compound obtained in Preparation 18.

EXAMPLE 19

N-{2-[7-(4-{[3-[(Acetylamino)ethyl]-2-(3-methoxybenzyl)-1-benzofuran-5-yl]amino}butoxy)-1-naphthyl]ethyl}-2-furamide The procedure is as for Example 18, in Step A replacing the compound of Preparation 1 by the compound of Preparation 19, and in Step D replacing the compound of Preparation 9 by the compound of Preparation 42.

EXAMPLE 20

N-({6-[4-({3-[(Acetylamino)ethyl]-2-benzyl-1H-pyrrolo[2,3-b]pyridin-5-yl}oxy)butoxy]-4a,8a-dihydro-2H-chromen-3-yl}methyl)butanamide The procedure is as for Example 18, in Step A replacing the compound of Preparation 1 by the compound of Preparation 15, and in Step D replacing the compound of Preparation 9 by the compound of Preparation 20.

EXAMPLE 21

N-(2-{5-[4-({3-[2-(Acetylamino)ethyl]-2-[4-(trifluoromethyl)benzyl]-1-benzothiophen-5-yl}thio)butoxy]-1H-pyrrolo[2,3-b]pyridin-3-yl}ethyl)-cyclopropanecarboxamide The procedure is as for Example 18, in Step A replacing the compound of Preparation 1 by the compound of Preparation 10, and in Step D replacing the compound of Preparation 9 by the compound of Preparation 38.

EXAMPLE 22

N-(2-{5-[4-({3-[(Acetylamino)methyl]-4a,8a-dihydro-2H-chromen-6-yl}oxy)butoxy]-1-benzothiophen-3-yl}ethyl)cyclohexanecarboxamide The procedure is as for Example 18, in Step A replacing the compound of Preparation 1 by the compound of Preparation 16, and in Step D replacing the compound of Preparation 9 by the compound of Preparation 21.

EXAMPLE 23

2,2,2-Trifluoro-N-(2-{5-[4-({3-[2-(hexylamino)-2-oxoethyl]-3a,7a-dihydro-1-benzofuran-5-yl}oxy)butoxy]-1-benzothiophen-3-yl}ethyl)-acetamide The procedure is as for Example 18, in Step A replacing the compound of Preparation 1 by the compound of Preparation 22, and in Step D replacing the compound of Preparation 9 by the compound of Preparation 23.

EXAMPLE 24

N-(2-{7-[4-({4-[2-(Acetylamino)ethyl]-3,4-dihydro-2H-chromen-6-yl}-oxy)butoxy]-1,2,3,4-tetrahydro-1-naphthalenyl}ethyl)acetamide The procedure is as for Example 18, in Step A replacing the compound of Preparation 1 by the compound of Preparation 24, and in Step D replacing the compound of Preparation 9 by the compound of Preparation 25.

EXAMPLE 25

N-{2-[5-({4-[(8-{2-[(Cyclopropylcarbonyl)amino]ethyl}-5,6,7,8-tetrahydro-2-naphthalenyl)oxy]butyl}amino)-1-benzofuran-3-yl]ethyl}-2-furamide The procedure is as for Example 18, in Step A replacing the compound of Preparation 1 by the compound of Preparation 26, and in Step D replacing the compound of Preparation 9 by the compound of Preparation 43.

EXAMPLE 26

N-(2-{5-[4-({8-[2-(Heptanoylamino)ethyl]-2-naphthyl}oxy)butoxy]-1H-indol-3-yl}ethyl)cyclobutanecarboxamide The procedure is as for Example 18, in Step A replacing the compound of Preparation 1 by the compound of Preparation 27, and in Step D replacing the compound of Preparation 9 by the compound of Preparation 28.

EXAMPLE 27

N-[2-(5-{[6-({8-[2-(Acetylamino)ethyl]-2-naphthyl}oxy)hexyl]oxy}-1H-pyrrolo[2,3-b]pyridin-3-yl)ethyl]acetamide Step A N-(2-{7-[(6-Hydroxyhexyl)oxy]-1-naphthyl}ethyl)acetamide The procedure is as for Step A of Example 12, replacing 3-bromopropan-1-ol by 6-bromohexan-1-ol. White solid.

Melting, point: 58–61° C.

Elemental microanalysis:

| % | C | H | N |
|---|---|---|---|
| Calculated: | 72.91 | 8.41 | 4.25 |
| Found: | 73.22 | 8.17 | 4.02 |

Step B: 6-({8-[2-(Acetylamino)ethyl]-2-naphthyl}oxy)hexyl methanesulphonate

The procedure is as for Step B of Example 12. White solid.

Melting point: 66–67° C.

Step C: N-[2-(5-{[6-({8-[2-(Acetylamino)ethyl]-2-naphthyl}oxy)hexyl]oxy}-1H-pyrrolo[2, 3-b]pyridin-3-yl)ethyl]acetamide The procedure is as for Step C of Example 12, replacing the compound obtained in Preparation 9 by the compound obtained in Preparation 12.

EXAMPLE 28

4-(7-{[6-({3-[(Acetylamino)methyl]-2H-chromen-6-yl}oxy)hexyl]oxy}-1-naphthyl)-N-isopropylbutanamide The procedure is as for Example 27, in Step A replacing the compound obtained in Preparation 1 by the compound obtained in Preparation 29, and in Step C replacing the compound obtained in Preparation 9 by the compound obtained in Preparation 16.

EXAMPLE 29

N-{[7-({6-[(3-{2-[(Anilinocarbonyl)amino]ethyl}-1-benzofuran-5-yl)-oxy]hexyl}oxy)-1,4-benzodioxin-2-yl]methyl}acetamide The procedure is as for Example 27, in Step A replacing the compound of Preparation 1 by the compound obtained in Preparation 30, and in Step C replacing the compound of Preparation 9 by the compound obtained in Preparation 18.

EXAMPLE 30

N-[2-(7-{[6-({3-[2-(Benzylamino)-2-oxoethyl]-1-benzothiophen-5-yl}oxy)hexyl]thio}-1,2,3,4-tetrahydro-1-naphthalenyl)ethyl]cyclopropanecarboxamide The procedure is as for Example 27, replacing:
in Step A, the compound of Preparation 1 by the compound of Preparation 31,
in Step C, the compound of Preparation 9 by the compound of Preparation 26.

EXAMPLE 31

N-[2-(5-{[6-({3-[3-(Methylamino)-3-oxopropyl]-2-benzofuran-5-yl}oxy)hexyl]oxy}-1H-inden-3-yl)ethyl]pentanamide The procedure is as for Example 17, in Step A replacing the compound of Preparation 1 by the compound of Preparation 32, and in Step C replacing the compound of Preparation 9 by the compound of Preparation 33.

EXAMPLE 32

N-Cyclopropyl-N'-(2-{5-[(6-{[3-(2-{[(methylamino)carbonyl]amino}-ethyl)-1H-pyrrolo[2,3-b]pyridin-5-yl]oxy}hexyl)amino]-1-benzofuran-3-yl}ethyl)urea The procedure is as for Example 27, in Step A replacing the compound of Preparation 1 by the compound of Preparation 34, and in Step C replacing the compound of Preparation 9 by the compound of Preparation 44.

EXAMPLE 33

N-[2-(7-{[6-({3-[4-(Methylamino)-4-oxobutyl]-1H-indol-5-yl}oxy)-hexyl]oxy}-1-naphthyl)ethyl]-3-butenamide The procedure is as for Example 27, replacing:
in Step A, the compound of Preparation 1 by the compound of Preparation 6,
in Step C, the compound of Preparation 9 by the compound of Preparation 35.

EXAMPLE 34

N-[2-(7-{3-[2-(Acetylamino)ethyl]-1-benzofuran-5-yl}-1-naphthyl)-ethyl]acetamide Under nitrogen, 2.76 mmol of the compound obtained in Preparation 45, 2.76 mmol of the compound obtained in Preparation 46, 1.94 mmol of dichlorobis(triphenylphosphine)nickel, 3.87 mmol of triphenylphosphine and 8.30 mmol of zinc are suspended in 20 ml of anhydrous DMF. After heating for 48 hours at 120° C. under nitrogen, the reaction mixture is concentrated and the resulting residue is partitioned between $CH_2Cl_2$ and M $NaHCO_3$. The organic phase is then dried over $Na_2SO_4$ and concentrated in vacuo. The title compound is separated off by chromatography over silica gel.

In Examples 35 to 48, the procedure is as for Example 34 starting from the appropriate Preparations.

EXAMPLE 35

N-(2-{5-[8-(2-{[(Methylamino)carbonyl]
amino}ethyl)-2-naphthyl]-1-benzothiophen-3-
yl}ethyl)cyclopropanecarboxamide Starting materials: Preparations 47 and 48

EXAMPLE 36

N-{2-[5-(3-{2-[(Anilinocarbonyl)amino]ethyl}-1-
benzofuran-5-yl)-1-benzothiophen-3-yl]ethyl}-2-
furamide Starting materials: Preparations 49 and 50

EXAMPLE 37

2-(5-{3-[2-(Acetylamino)ethyl]-1-benzofuran-5-yl}-
1H-indol-3-yl)-N-benzylacetamide Starting materials: Preparations 45 and 51

EXAMPLE 38

N-[3-(5-{3-[2-(Isobutyrylamino)ethyl]-1-
benzothiophen-5-yl}-1H-indol-3-yl)propyl]
benzamide Starting materials: Preparations 52 and 53

EXAMPLE 39

N-[3-(5-{8-[2-(Acetylamino)ethyl]-2-naphthyl}-1H-
pyrrolo[2,3-b]-pyridin-3-yl)propyl]heptanamide Starting materials: Preparations 46 and 54

EXAMPLE 40

4-(5-{3-[3-(Acetylamino)ethyl]-1H-pyrrolo[2,3-b]
pyridin-5-yl}-1-benzofuran-3-yl)-N-
cyclopentylbutanamide Starting materials: Preparations 55 and 56

EXAMPLE 41

N-(2-{5-[3-(2-{[(Allylamino)carbonyl]
amino}ethyl)-1-benzothiophen-5-yl]-1H-pyrrolo[2,
3-b]pyridin-3-yl}ethyl)cyclopropanecarboxamide Starting materials: Preparations 57 and 58

EXAMPLE 42

N-[2-(5-{3-[(Acetylamino)methyl]-1,4-benzodioxin-
6-yl}-1H-pyrrolo[2,3-b]pyridin-3-yl)ethyl]
cyclopropanecarboxamide Starting materials: Preparations 57 and 59

EXAMPLE 43

2-Methyl-N-{2-[5-(4-{2-[(2,2,2-trifluoroacetyl)
amino]ethyl}-3,4-dihydro-2H-chromen-6-yl)-1-
benzofuran-3-yl]ethyl}propanamide Starting materials: Preparations 60 and 61

EXAMPLE 44

4-(5-{3-[(Acetylamino)methyl]-3,4-dihydro-2H-
chromen-6-yl-}-1-benzothiophen-3-yl)-N-
phenylbutanamide Starting materials: Preparations 62 and 63

EXAMPLE 45

N-(2-{5-{8-[2-(Acetylamino)ethyl]-2-naphthyl}-2-
[4-(trifluoromethyl)-benzyl]-1-benzofuran-3-
yl}ethyl)acetamide Starting materials: Preparations 64 and 46

EXAMPLE 46

2,2-Dimethyl-N-(2-{6-[3-(2-{[(methylamino)
carbonyl]amino}ethyl)-1H-indol-5-yl]-3,4-dihydro-
2H-chromen-4-yl}ethyl)propanamide Starting materials: Preparations 65 and 66

EXAMPLE 47

N-[(7-{3-[2-(Acetylamino)ethyl]-1H-indol-5-yl}-1,
4-benzodioxin-2-yl)-methyl]
cyclohexanecarboxamide Starting materials: Preparations 67 and 68

EXAMPLE 48

N-(3-{5-[3-[2-(Acetylamino)ethyl]-2-(3-
methoxybenzyl)-1-benzothiophen-5-yl]-1-
benzofuran-3-yl}propyl)acetamide Starting materials: Preparations 69 and 70

EXAMPLE 49

N-(2-{7-[4-({3-[2-(Acetylamino)ethyl]-1-
benzofuran-5-yl}oxy)butoxy]-1-naphthyl}ethyl)
acetamide Step A: N-{2-[7-(4-Bromobutoxy)-1-naphthyl]
ethyl}acetamide In a 100 ml round-bottomed flask, 10 mmol of the compound obtained in Preparation 1 are dissolved in 50 ml of acetonitrile. 30 mmol of potassium carbonate are added and the mixture is stirred at reflux using a magnetic stirrer for 30 minutes, and then 10 mmol of 1,4-dibromobutane are added. After 12 hours at reflux, the acetonitrile is removed by evaporation in vacuo and the resulting residue is taken up in a 1M sodium hydroxide solution. The resulting precipitate is filtered off and recrystallised to yield the title product.

Step B: N-(2-{7-[4-({3-[2-(Acetylamino)ethyl]-1-
benzofuran-5-yl}oxy)butoxy]-1-naphthyl}ethyl)acetamide In a 100 ml round-bottomed flask containing 30 ml of methanol, sodium (0.07 g; 0.0030 at.g) is added in small portions. When the sodium has been completely used up, 3.6 nnol of the compound obtained in Preparation 2 are added. After stirring for 20 minutes, the methanol is removed by evaporation under reduced pressure. and the residue is taken up in 15 ml of DMF. 3 mmol of the compound obtained in Step A are added, and the mixture is refluxed for 12 hours. The reaction mixture is cooled and poured into a mixture of 100 ml of water and 10 ml of 3M hydrochloric acid. Extraction of the aqueous phase is carried out twice with ethyl acetate, and the organic phase is washed with a 10% sodium hydroxide solution and then with water. The resulting solid is recrystallised from acetonitrile to yield the title product.

Melting point: 160–162° C.

EXAMPLE 50

N-{2-[5-[4-({8-[2-(Acetylamino)ethyl]-2-
naphthyl}oxy)butoxy]-1-(phenylsulphonyl)-1H-
indol-3-yl]ethyl}acetamide In a 100 ml round-bottomed flask, 10 mmol of the compound obtained in Preparation 71 are dissolved in 50 ml of acetonitrile, and then 4.17 g of potassium carbonate are added and the reaction mixture is stirred at reflux using a magnetic stirrer for 30 minutes. 10 mmol of the compound obtained in Step A of Example 49 are then added and the mixture is heated at reflux for 12 hours. The acetonitrile is removed by evaporation in vacuo and the resulting residue is taken up in an aqueous 1M sodium hydroxide solution. The resulting precipitate is filtered off and recrystallised from alcohol at 95°.

Melting point: 135–137° C.

EXAMPLE 51

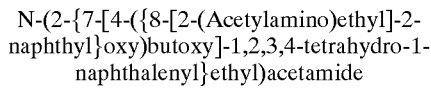
N-(2-{7-[4-({8-[2-(Acetylamino)ethyl]-2-naphthyl}oxy)butoxy]-1,2,3,4-tetrahydro-1-naphthalenyl}ethyl)acetamide The procedure is as for Example 49, in Step B replacing the product obtained in Preparation 2 by the product obtained in Preparation 25. Recrystallisation from acetonitrile.

Melting point: 63–65° C.

EXAMPLE 52

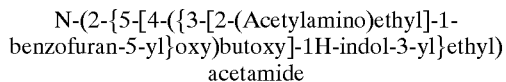
N-(2-{5-[4-({3-[2-(Acetylamino)ethyl]-1-benzofuran-5-yl}oxy)butoxy]-1H-indol-3-yl}ethyl)acetamide Step A : Ethyl 4-({3-[2-(acetylamino)ethyl]-1H-indol-5-yl}oxy)butanoate 5.9 g of the compound obtained in Preparation 11 are dissolved in 100 ml of acetonitrile. and then 11.22 g of potassium carbonate and 5.81 ml of ethyl 4-bromobutanoate are added. After refluxing overnight, the potassium carbonate is filtered off, the acetonitrile is removed by evaporation and the residue is taken up in 100 ml of water. Extraction is carried out three times with 50 ml of ethyl acetate each time, and the organic phase is then washed with water to neutral pH, dried over magnesium sulphate and evaporated in vacuo. The resulting oil precipitates from isopropyl ether.

Melting point: 107–108° C.

Step B: N-{2-[5-(4-Hydroxybutoxy)-1H-indol-3-yl]ethyl}acetamide

A solution of 6.2 g of the compound obtained in Step A in 50 ml of anhydrous THF is added dropwise to a suspension of 1.42 g of lithium aluminum hydride in 50 ml of anhydrous THF cooled in an ice-bath. After stirring for 30 minutes at room temperature, a solution of 5% sodium hydroxide is added dropwise until the evolution of gas ceases. The precipitate that forms is filtered off, the organic phase is evaporated and the residue is taken up in 70 ml of ethyl acetate. The organic phase is washed with water until neutrality, dried over magnesium sulphate and evaporated in vacuo to yield the title product in the form of an oil.

Step C: N-{2-[5-(4-Bromobutoxy)-1H-indol-3-yl]ethyl}acetamide 3.92 g of the compound obtained in Step B are dissolved in 50 ml of acetonitrile, and then 5.31 g of triphenylphosphine and 6.71 g of carbon tetrabromide are added with stirring. After leaving at room temperature overnight, the acetonitrile is removed by evaporation in vacuo and the resulting residue is purified by chromatography over a column of silica gel (eluant: dichloromethane/methanol 96/4). Oil.

Step D: N-(2-{5-[4-({3-[2-(Acetylamino)ethyl]-1-benzofuran-5-yl}oxy)butoxy]-1-indol-3-yl}ethyl)acetamide 0.72 g of the compound obtained in Step C is dissolved in 20 ml of acetonitrile, and then 0.57 g of potassium carbonate and 0.30 g of the compound obtained in Preparation 2 are added. After being refluxed overnight, the reaction mixture is poured into 200 ml of water and ice. The resulting precipitate is filtered off, washed with ether, dried and recrystallised to yield the title product in the form of a white powder.

Melting point: 164–166° C.

EXAMPLE 53

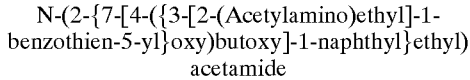
N-(2-{7-[4-({3-[2-(Acetylamino)ethyl]-1-benzothien-5-yl}oxy)butoxy]-1-naphthyl}ethyl)acetamide The procedure is as for Example 49, in Step B replacing the product obtained in Preparation 2 by the product obtained in Preparation 9. Recrystallisation from acetonitrile/methanol (2/1).

Melting point: 169–170° C.

EXAMPLE 54

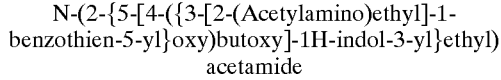
N-(2-{5-[4-({3-[2-(Acetylamino)ethyl]-1-benzothien-5-yl}oxy)butoxy]-1H-indol-3-yl}ethyl)acetamide The procedure is as for Example 49, in Step A replacing the product obtained in Preparation 1 by the product obtained in Preparation 9 and in Step B replacing the product obtained in Preparation 2 by the product obtained in Preparation 11.

EXAMPLE 55

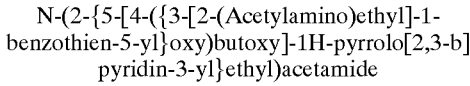
N-(2-{5-[4-({3-[2-(Acetylamino)ethyl]-1-benzothien-5-yl}oxy)butoxy]-1H-pyrrolo[2,3-b]pyridin-3-yl}ethyl)acetamide The procedure is as for Example 49, in Step A replacing the product obtained in Preparation 1 by the product obtained in Preparation 9 and in Step B replacing the product obtained in Preparation 2 by the product obtained in Preparation 12.

EXAMPLE 56

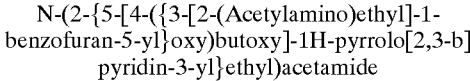
N-(2-{5-[4-({3-[2-(Acetylamino)ethyl]-1-benzofuran-5-yl}oxy)butoxy]-1H-pyrrolo[2,3-b]pyridin-3-yl}ethyl)acetamide The procedure is as for Example 49, in Step A replacing the product obtained in Preparation 1 by the product obtained in Preparation 2 and in Step B replacing the product obtained in Preparation 2 by the product obtained in Preparation 12.

EXAMPLE 57

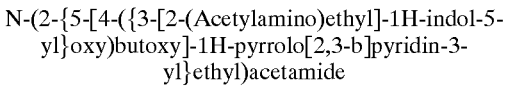
N-(2-{5-[4-({3-[2-(Acetylamino)ethyl]-1H-indol-5-yl}oxy)butoxy]-1H-pyrrolo[2,3-b]pyridin-3-yl}ethyl)acetamide The procedure is as for Example 49, in Step A replacing the product obtained in Preparation 1 by the product obtained in Preparation 11 and in Step B replacing the product obtained in Preparation 2 by the product obtained in Preparation 12.

Examples 58 to 64 are obtained by proceeding as for Example 34 starting from the appropriate Preparations.

EXAMPLE 58

N-[2-(7-{3-[2-(Acetylamino)ethyl]-1-benzothien-5-yl}-1-naphthyl)ethyl]acetamide

Starting materials: Preparations 46 and 72.

EXAMPLE 59

N-[2-(5-{8-[2-(Acetylamino)ethyl]-2-naphthyl}-1H-pyrrolo[2,3-b]-pyridin-3-yl)ethyl]acetamide Starting materials: Preparations 46 and 55.

EXAMPLE 60

N-[2-(5-{3-[2-(Acetylamino)ethyl]-1-benzofuran-5-yl}-1-benzothien-3-yl)ethyl]acetamide Starting materials: Preparations 72 and 45.

EXAMPLE 61

N-[2-(5-{3-[2-(Acetylamino)ethyl]-1-benzofuran-5-yl}-1H-indol-3-yl)ethyl]acetamide Starting materials: Preparations 67 and 45.

EXAMPLE 62

N-[2-(5-{3-[2-(Acetylamino)ethyl]-1-benzofuran-5-yl}-1H-pyrrolo-[2,3-b]pyridin-3-yl)ethyl]acetamide Starting materials: Preparations 55 and 45.

EXAMPLE 63

N-[2-(5-{3-[2-(Acetylamino)ethyl]-1H-indol-5-yl}-1H-pyrrolo-[2,3-b]pyridin-3-yl)ethyl]acetamide Starting materials: Preparations 55 and 67.

EXAMPLE 64

N-[2-(5-{3-[2-(Acetylamino)ethyl]-1-benzothien-5-yl}-1H-pyrrolo-[2,3-b]pyridin-3-yl)ethyl]acetamide Starting materials: Preparations 55 and 72.

Pharmacological Study

Example A: Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (the dose that causes the death of 50% of the animals) was evaluated and demonstrated the low toxicity of the compounds of the invention.

Example B: Melatonin Receptor Binding Study on Pars Tuberalis Cells of Sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol

1) Sheep pars tuberalis membranes are prepared and used as target tissue in saturation experiments to determine the binding capacities and affinities for 2-[$^{125}$I]-iodomelatonin.

2) Sheep pars tuberalis membranes are used as target tissue in competitive binding experiments using the various test compounds in comparison with melatonin.

Each experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

Example C: Melatonin $mt_1$ and $MT_2$ Receptor Binding Study

The $mt_1$ or $MT_2$ receptor binding experiments are carried out using 2-[$^{125}$I]-iodomelatonin as reference radioligand. The radioactivity retained is determined using a liquid scintillation counter.

Competitive binding experiments are then carried out in triplicate using the various test compounds. A range of different concentrations is tested for each compound. The results enable the binding affinities of the compounds tested ($IC_{50}$) to be determined.

Thus, the $IC_{50}$ values found for the compounds of the invention show binding for one or other of the $mt_1$ and $MT_2$ receptor sub-types, those values being <10 $\mu$M.

Example D: Action of the Compounds of the Invention on the Circadian Rhythms of Locomotive Activity of the Rat The involvement of melatonin in influencing the majority of physiological, biochemical and behavioural circadian rhythms by day/night alternation has made it possible to establish a pharmacological model for research into melatoninergic ligands.

The effects of the compounds are tested in relation to numerous parameters and, in particular, in relation to the circadian rhythms of locomotive activity, which are a reliable indicator of the activity of the endogenous circadian clock.

In this study, the effects of such compounds on a particular experimental model, namely the rat placed in temporal isolation (permanent darkness) are evaluated.

Experimental Protocol

One-month-old male rats are subjected, as soon as they arrive at the laboratory, to a light cycle of 12 hours of light per 24 hours (LD 12:12). After 2 to 3 weeks' adaptation, they are placed in cages fitted with a wheel connected to a recording system in order to detect the phases of locomotive activity and thus monitor the nychthemeral (LD) or circadian (DD) rhythms.

As soon as the rhythms recorded show a stable pattern in the light cycle LD 12:12, the rats are placed in permanent darkness (DD).

Two to three weeks later, when the free course (rhythm reflecting that of the endogenous clock) is clearly established, the rats are given a daily administration of the compound to be tested.

The observations are made by means of visualisation of the rhythms of activity:

influence of the light rhythm on the rhythms of activity, disappearance of the influence on the rhythms in permanent darkness, influence by the daily administration of the compound; transitory or durable effect.

A software package makes it possible:

to measure the duration and intensity of the activity, the period of the rhythm of the animals during free course and during treatment, possibly to demonstrate by spectral analysis the existence of circadian and non-circadian (for example ultradian) components.

Results

The compounds of the invention clearly appear to have a powerful action on the circadian rhythm via the melatoninergic system.

Example E: Light/Dark Cage Test

The compounds of the invention are tested on a behavioural model, the light/dark cage test, which enables the anxiolytic activity of the compounds to be revealed.

The equipment comprises two polyvinyl boxes covered with Plexiglas. One of the boxes is in darkness. A lamp is placed above the other box, yielding a light intensity of approximately 4000 lux at the centre of the box. An opaque plastic tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

After administration of the compounds 30 minutes before the start of the test, the compounds of the invention significantly increase the time spent in the illuminated cage and the number of passages through the tunnel, which demonstrates the anxiolytic activity of the compounds of the invention.

Example F: Activity of the Compounds of the Invention on the Caudal Artery of the Rat The compounds of the invention were tested in vitro on the caudal artery of the rat. Melatoninergic receptors are present in those vessels, thus providing a relevant pharmacological model for studying melatoninergic ligand activity. The stimulation of the receptors can induce either vasoconstriction or dilation depending upon the arterial segment studied.

Protocol

One-month-old rats are accustomed to a light/dark cycle of 12 h/12 h during a period of 2 to 3 weeks.

After sacrifice, the caudal artery is isolated and maintained in a highly oxygenated medium. The arteries are then cannulated at both ends, suspended vertically in an organ chamber in a suitable medium and perfused via their proximal end. The pressure changes in the perfusion flow enable evaluation of the vasoconstrictive or vasodilatory effect of the compounds.

The activity of the compounds is evaluated on segments that have been pre-contracted by phenylephrine (1 $\mu$M). A concentration/response curve is determined non-cumulatively by the addition of a concentration of the test compound to the pre-contracted segment. When the effect observed reaches equilibrium, the medium is changed and the preparation is left for 20 minutes before the addition of the same concentration of phenylephrine and a further concentration of the test compound.

Results

The compounds of the invention significantly modify the diameter of caudal arteries pre-constricted by phenylephrine.

Example G: Pharmaceutical Composition:Tablets

| 1000 tablets containing a dose of 5 mg of N-(2-{7-[4-({3-[2-(acetylamino)ethyl]-1-benzofuran-5-yl}oxy)butoxy]-1-naphthyl}ethyl)acetamide (Example 49) | 5 g |
|---|---|
| Wheat starch | 20 g |
| Maize starch | 20 g |
| Lactose | 30 g |
| Magnesium stearate | 2 g |
| Silica | 1 g |
| Hydroxypropyl cellulose | 2 g |

What is claimed is:

1. A compound selected from those of formula (I):

$$A—G_1—Cy—G_2—Cy'—G_3—B \qquad (I)$$

wherein:

A represents a grouping of formula

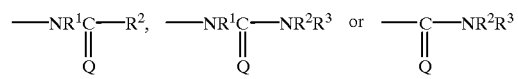

wherein:

Q represents sulphur or oxygen, $R^1$, $R^2$, and $R^3$ which may be identical or different, represent hydrogen or $R_a$, wherein $R_a$ represents unsubstituted or substituted linear or branched ($C_1$–$C_6$)alkyl, unsubstituted or substituted linear or branched ($C_2$–$C_6$)alkenyl, unsubstituted or substituted linear or branched ($C_2$–$C_6$)alkynyl, unsubstituted or substituted ($C_3$–$C_8$)-cycloalkyl, unsubstituted or substituted cycloalkyl-($C_3$–$C_8$)alkyl in which the alkyl moiety is linear or branched, polyhalo-($C_1$–$C_6$)alkyl in which the alkyl moiety is linear or branched, aryl, aryl-($C_1$–$C_6$)alkyl in which the alkyl moiety is linear or branched, aryl-($C_2$–$C_6$) alkenyl in which the alkenyl moiety is linear or branched, heteroaryl, heteroaryl-($C_1$–$C_6$)alkyl in which the alkyl moiety is linear or branched or heteroaryl-($C_2$–$C_6$)alkenyl in which the alkenyl moiety is linear or branched, or $R^2$ and $R^3$ can also form with the nitrogen atom carrying them a group selected from piperazinyl, piperidinyl and pyrrolidinyl, B represents a grouping of formula

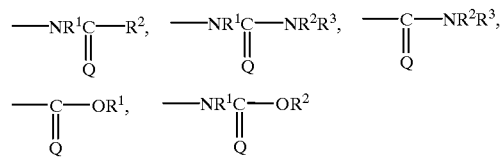

or —NR²R³, wherein Q, $R^1$, $R^2$, and $R^3$ are as defined hereinbefore, $G_1$ and $G_3$, which may be identical or different, represent a linear or branched alkylene chain containing 1 to 4 carbon atoms that are optionally substituted by one or more identical or different groups selected from hydroxy, carboxy, formyl, $R_a$, $OR_a$, $COOR_a$ and $COR_a$, wherein $R_a$ is as defined hereinbefore, Cy and Cy', which are different, represent a ring structure of formula (II):

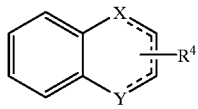

(II)

wherein:
X and Y, which may be identical or different, represent sulphur, oxygen or carbon, or CH or $CH_2$,
$R^4$ represents hydrogen or halogen, or $CF_3$, hydrogen, carboxy, formyl, amino, $NHR_a$, $NR_aR^1_a$, $NHCOR_a$, $CONHR_a$, $R_a$, $OR_a$, $COR_a$ or $COOR_a$, wherein $R_a$ is as defined herein before and $R^1_a$ can have any of the meanings of $R_a$,
the symbol === means that the bonds are single or double, with the proviso that he valency of the atoms is respected,
wherein $G_2$ substitutes the benzene ring, and $G_1$ substitutes the ring containing X and Y in the case of Cy, and $G_2$ substitutes the benzene ring and $G_3$ substitutes the ring containing X and Y in the case of Cy',
or a ring structure of formula (III):

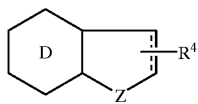

(III)

wherein:
Z represents sulphur or oxygen, or $CH_2$, NH, $NSO_2Ph$ or $NR_a$ wherein $R_a$ is as defined hereinbefore,
D represents a benzene or pyridine ring,
$R^4$ is as defined hereinbefore,
the symbol === means that the bond is single or double, with the proviso that the valency of the atoms is respected,
wherein $G_2$ substitutes the D ring, and $G_1$ substitutes the ring containing Z in the case of Cy, and $G_2$ substitutes the D ring and $G_3$ substitutes the ring containing Z in the case of Cy',
the two different rings Cy and Cy' of the compounds of formula (I) both being represented by a structure of formula (II) or by a structure of formula (III), or one of the two rings being represented by a structure of formula (II) and the other being represented by a structure of formula (III),
$G_2$ represents a chain of formula (IV):

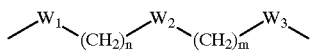

(IV)

wherein:
$W_1$, $W_2$, and $W_3$, which may be identical or different, represent a bond, oxygen or sulfur, or $CH_2$, $CHR_a$, NH, or $NR_a$, wherein $R_a$ is as defined hereinbefore,
n represents an integer wherein $0 \leq n \leq 6$,
m represents an integer wherein $0 \leq m \leq 6$,
with the proviso that it is not possible to have two consecutive hetero atoms and that the chain of formula (IV) so defined may have one or more unsaturated bonds,
it being understood that:
"aryl" is naphthyl, phenyl, or biphenyl,
"heteroaryl" is a saturated or unsaturated mono- or bi-cyclic group containing 5 to 10 ring atoms and containing 1 to 3 hetero atoms selected from nitrogen, sulphur, and oxygen,
it being possible for "aryl" and "heteroaryl" to be substituted by one or more identical or different radicals selected from hydroxy, carboxy, linear or branched $(C_1-C_6)$alkoxy, linear or branched $(C_1-C_6)$ alkyl, polyhalo-$(C_1-C_6)$alkyl in which the alkyl moiety is linear or branched, formyl, cyano, nitro, amino, linear or branched $(C_1-C_6)$alkylamino, di-$(C_1-C_6)$alkylamino in which each alkyl moiety is linear or branched, and halogen,
the term "substituted" applied to the terms "alkyl", "alkenyl", and "alkynyl" means that those groups are substituted by one or more identical or different radicals selected from hydroxy, linear or branched $(C_1-C_6)$alkoxy, polyhalo-$(C_1-C_6)$alkyl in which the alkyl moiety is linear or branched, amino, linear or branched $(C_1-C_6)$alkylamino, di-$(C_1-C_6)$alkylamino in which each alkyl moiety is linear or branched, and halogen,
the term "substituted" applied to the terms "cycloalkyl" and "cycloalkylalkyl" means that the cyclic moiety of those groups is substituted by one or more identical or different radicals selected from hydroxy, linear or branched $(C_1-C_6)$alkoxy, polyhalo-$(C_1-C_6)$ alkyl in which the alkyl moiety is linear or branched, amino, linear or branched $(C_1-C_6)$alkylamino, di-$(C_1-C_6)$alkylamino in which each alkyl moiety is linear or branched, and halogen,
its enantiomers and diasterioisomers, and addition salts thereof with a pharmaceutically-acceptable acid or base.

2. A compound of claim 1 wherein Cy and Cy', which are different, represent a ring structure of formula (II).

3. A compound of claim 1 wherein Cy and Cy', which are different, represent a ring structure of formula (III).

4. A compound of claim 1 wherein Cy represents a ring structure of formula (II) and Cy' represents a ring structure of formula (III).

5. A compound of claim 1 wherein $G_2$ represents a single bond.

6. A compound of claim 1 wherein $G_2$ represents —$W_4$—$(CH_2)_p$—$W'_4$— wherein $W_4$ and $W'_4$, which may be identical or different, represent oxygen or sulphur or NH or $NR_a$, and p represents an integer wherein $1 \leq p \leq 12$.

7. A compound of claim 1 wherein $G_2$ represents —O—$(CH_2)_p$—O— wherein p represents an integer wherein $1 \leq p \leq 12$.

8. A compound of claim 1 wherein A and B, which may be identical or different, represent $NR^1COR^2$ or $CONR^2R^3$.

9. A compound of claim 1 which is selected from N-(2-{7-[2-({3-[2-(acetylamino)ethyl]-1-benzofuran-5-yl}oxy)ethoxy]-1-naphthyl}ethyl)acetamide, N-(2-{5-[2-({8-[2-(acetylamino)ethyl]-2-naphthyl}oxy)ethoxy-1-benzofuran-3-yl}ethyl)-2-furamide, N-(2-{5-[2-({8-[2-(acetylamino)ethyl]-2-naphthyl}oxy)ethoxy]-1H-pyrrolo[2,3-b]pyridin-3-yl}ethyl)cyclopropanecarboxamide, N-(2-{7-[3-({3-[2-(acetylamino)-ethyl]-1-benzothiophen-5-yl}oxy)propoxy]-1-naphthyl}ethyl)acetamide, N-[2-(5-{[6-({8-[2-(acetylamino)ethyl]-2-naphthyl}oxy)hexyl]oxy}-1H-pyrrolo[2,3-b]pyridin-3-yl)ethyl]-acetamide, N-(2-{5-[4-

({3-[2-(acetylamino)ethyl]-1-benzothien-5-yl}oxy)butoxy]-1H-indol-3-yl}ethyl)acetamide, N-(2-{5-[4-({3-[2-(acetylamino)ethyl]-1-benzothien-5-yl}-oxy)butoxy]-1H-pyrrolo[2,3-b]pyridin-3-yl}ethyl)acetamide, N-(2-{5-[4-({3-[2-acetyl-amino)ethyl]-1-benzofuran-5-yl }oxy)butoxy]-1H-pyrrolo[2,3-b]pyridin-3-yl}ethyl)-acetamide, N-(2-{5-[4-({3-[2-(acetylamino)ethyl]-1H-indol-5-yl}oxy)butoxy]-1H-pyrrolo[2,3-b]pyridin-3-yl}ethyl)acetamide, and addition salts of any of the foregoing with a pharmaceutically foregoing acceptable acid or base.

10. A compound of claim 1 which is selected from N-(2-{7-[4-({3-[2-(acetylamino)ethyl]-1-benzofuran-5-yl}oxy)butoxy]-1-naphthyl}ethyl)acetamide, N-{2-[5-[4-({8-[2-(acetylamino)ethyl]-2-naphthyl}oxy)butoxy]-1-(phenylsulphonyl)-1H-indol-3-yl]ethyl}acetamide, N-(2-{7-[4-({8-[2-(acetylamino)ethyl]-2-naphthyl}oxy)butoxy]-1,2,3,4-tetrahydro- 1-naphthalenyl}ethyl)acetamide, N-(2-{5-[4-({3-[2-(acetylamino)ethyl]-1-benzofuran-5-yl }oxy)butoxy]-1H-indol-3-yl}ethyl)acetamide, N-(2-{7-[4-({3-[2-(acetyl-amino)ethyl]-1-benzothien-5-yl}oxy)butoxy]-1-naphthyl}ethyl)acetamide, and addition salts of any of the foregoing with a pharmaceutically acceptable acid or base.

11. A compound of claim 1 which is selected from N-[2-(7-{3-[2-(acetylamino)ethyl]-1-benzofuran-5-yl}-1-naphthyl)ethyl]acetamide, N-[3-(5-{8-[2-(acetylamino) ethyl]-2-naphthyl}-1H-pyrrolo[2,3-b]pyridin-3-yl)propyl] heptanamide, N-[2-(7-{3[-2-(acetylamino)ethyl]-1-benzothien-5-yl}-1-naphthyl)ethyl]acetamide, N-[2-(5-{8-[2-(acetylamino)ethyl]-2-naphthyl}-1H-pyrrolo[2,3-b] pyridin-3-yl)ethyl]acetamide, N-[2-(5-{3-[2-(acetylamino) ethyl]-1-benzofuran-5-yl}-1-benzothien-3-yl)ethyl] acetamide, N-[2-(5-{3-[2-(acetylamino)ethyl]-1-benzofuran-5-yl }-1H-indol-3-yl)ethyl]acetamide, N-[2-(5-{3-[2-(acetylamino)ethyl]-1-benzofuran-5-yl}-1H-pyrrolo [2,3-b]pyridin-3-yl)ethyl]-acetamide, N-[2-(5-{3-[2-(acetylamino)ethyl]-1H-indol-5-yl}-1H-pyrrolo[2,3-b] pyridin-3-yl)ethyl]acetamide, N-[2-(5-{3-[2-(acetylamino) ethyl]-1-benzothien-5-yl }-1H-pyrrolo-[2,3-b]pyridin-3-yl) ethyl]acetamide, and addition salts of any of the foregoing with a pharmaceutically acceptable acid or base.

12. A method of treating a living body afflicted with a disorder of the melatoninergic system comprising the step of administering to the living body an amount of a compound of claim 1 which is effective for the alleviation of said disorder.

13. A pharmaceutical composition useful for treating melatoninergic disorders comprising, as active principle, an effective amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO.   : 6,310,074 B1
DATED        : October 30, 2001
INVENTOR(S)  : Patrick Depreux et al.

It is certified that error appears in the above-identified patent and that said Letters Patent is hereby corrected as shown below:

Column 36,
Line 60, "oxy)ethoxy" should read -- oxy)ethoxy] --.

Column 37,
Line 10, "foregoing" should be removed.
Line 22, "pharmaceutically acceptable" should read -- pharmaceutically-acceptable --.

Column 38,
Line 1, "N-[2-(7-{3[-2-(acetylamino)" should read -- N-[2-(7-{3-[2-(acetylamino) --.
Line 14, "pharmaceutically acceptable" should read -- pharmaceutically-acceptable --.
Line 23, "pharmaceutically acceptable" should read -- pharmaceutically-acceptable --.

Signed and Sealed this

Twelfth Day of March, 2002

Attest:

JAMES E. ROGAN
*Director of the United States Patent and Trademark Office*

*Attesting Officer*